(12) United States Patent
Kakkis

(10) Patent No.: US 9,241,896 B2
(45) Date of Patent: Jan. 26, 2016

(54) METHODS AND FORMULATIONS FOR TREATING SIALIC ACID DEFICIENCIES

(71) Applicant: ULTRAGENYX PHARMACEUTICAL INC., Novato, CA (US)

(72) Inventor: Emil Kakkis, San Rafael, CA (US)

(73) Assignee: ULTRAGENYX PHARMACEUTICAL INC., Novato, CA (US)

( * ) Notice: Subject to any disclaimer, the term of this patent is extended or adjusted under 35 U.S.C. 154(b) by 0 days.

(21) Appl. No.: 13/659,540

(22) Filed: Oct. 24, 2012

(65) Prior Publication Data

US 2013/0109637 A1 May 2, 2013

Related U.S. Application Data

(63) Continuation-in-part of application No. PCT/US2011/043910, filed on Jul. 13, 2011.

(60) Provisional application No. 61/363,995, filed on Jul. 13, 2010.

(51) Int. Cl.
| A61K 31/70 | (2006.01) |
|---|---|
| A61K 9/00 | (2006.01) |
| A61K 9/20 | (2006.01) |
| A61K 31/7012 | (2006.01) |

(52) U.S. Cl.
CPC .............. *A61K 9/0002* (2013.01); *A61K 9/205* (2013.01); *A61K 9/2054* (2013.01); *A61K 31/7012* (2013.01)

(58) Field of Classification Search
USPC ..................................................... 514/23, 25
See application file for complete search history.

(56) References Cited

U.S. PATENT DOCUMENTS

| 4,698,332 | A | * | 10/1987 | Ogasawara et al. ............. 514/42 |
|---|---|---|---|---|
| 5,624,677 | A | | 4/1997 | El-Rashidy et al. |
| 5,747,475 | A | | 5/1998 | Nordquist et al. |
| 6,444,649 | B1 | * | 9/2002 | Inamori et al. ................... 514/42 |
| 8,524,772 | B2 | | 9/2013 | Arad et al. |
| 8,840,926 | B2 | | 9/2014 | Kaskkis et al. |
| 2004/0192642 | A1 | | 9/2004 | Yang et al. |
| 2008/0085306 | A1 | | 4/2008 | Nangia et al. |
| 2008/0260824 | A1 | | 10/2008 | Nangia et al. |
| 2010/0159001 | A1 | * | 6/2010 | Cardinal et al. ............. 424/457 |
| 2010/0160363 | A1 | | 6/2010 | Cardinal et al. |
| 2010/0226855 | A1 | | 9/2010 | Nangia et al. |
| 2012/0264928 | A1 | | 10/2012 | Noguchi et al. |
| 2013/0122094 | A1 | | 5/2013 | Kakkis |
| 2013/0225513 | A1 | | 8/2013 | Kakkis |
| 2013/0273160 | A1 | | 10/2013 | Kakkis |
| 2015/0038693 | A1 | | 2/2015 | Kakkis et al. |

FOREIGN PATENT DOCUMENTS

| EP | 2332552 | 6/2011 |
|---|---|---|
| WO | WO 2004/000366 | 12/2003 |
| WO | WO 2006/096161 | 9/2006 |
| WO | WO 2008/150477 | 12/2008 |
| WO | WO 2009/032605 | 3/2009 |
| WO | WO 2010/131712 | 11/2010 |
| WO | WO 2012/009474 | 1/2012 |
| WO | WO 2013/063149 | 5/2013 |
| WO | WO 2013/109906 | 7/2013 |

OTHER PUBLICATIONS

Office Action for U.S. Appl. No. 13/659,550, mailed Oct. 7, 2013.
International Search Report and Written Opinion for International U.S. Appl. No. PCT/US2012/061737, mailed Mar. 15, 2013.
Office Action for Australian Application No. 2011279158, dated Oct. 23, 2013.
Supplementary European Search Report for European Application No. 11807478, mailed Dec. 5, 2013.
International Search Report and Written Opinion for International Application No. PCT/US2011/043910, mailed Oct. 18, 2011.
Aich, U. et al, "Development of Delivery Methods for Carbohydrate-based Drugs: Controlled Release of Biologically-Active Short Chain Fatty Acid-Hexosamine Analogs," Glycoconjugate Journal, 27(4):445-459 (2010).
Allevi, P. et al., "Chemoselective synthesis of sialic acid 1,7-lactones," J. Org. Chem., 75(16):5542-5548 (2010).
Argov, Z. et al., "Hereditary inclusion body myopathy. The Middle Eastern genetic cluster," Neurology, 60(9):1519-1523 (2003).
Askanas, V. et al., "Sporadic inclusion-body myositis and hereditary inclusion-body myopathies: current concepts of diagnosis and pathogenesis," Curr. Opin. Rheumatol., 10:530-542 (1998).
Broccolini, A. et al., "Novel GNE mutations in Italian families with autosomal recessive hereditary inclusion-body myopathy," Human Mutation, 23(6):632 (2004).
Rezende, M. C. et al., "A facile route to 9-phosphorylated neuraminic acid derivatives," Synthetic Communications, 28(23):4393-4400 (1998).
Colombo, R. et al., "The first synthesis of N-acetylneuraminic acid 1,7-lactone," Chem. Commun., 43:5517-5519 (2008).
Eisenberg, I. et al., "The UDP-N-acetylglucosamine 2-epimerase/N-acetylmannosamine kinase gene is mutated in recessive hereditary inclusion body myopathy," Nat. Genet., 29(1):83-87 (2001).
Frost, R. A. et al., "Regulation of insulin-like growth factor-I in skeletal muscle and muscle cells," Minerva Endocrinol., 28(1):53-73 (2003).
Galeano, B. et al., "Mutation in the key enzyme of sialic acid biosynthesis causes severe glomerular proteinuria and is rescued by N-acetylmannosamine," The Journal of Clinical Investigation, 117(6):1585-1594 (2007).

*Primary Examiner* — Adam C Milligan
(74) *Attorney, Agent, or Firm* — Cooley LLP

(57) ABSTRACT

Extended release formulations, methods of making, and methods of use, for example, in treatment of sialic acid deficiencies.

12 Claims, 7 Drawing Sheets

(56) References Cited

OTHER PUBLICATIONS

Jay, C. M. et al., "Hereditary Inclusion Body Myopathy (HIBM2)," Gene Regulation and Systems Biology, 3:181-190 (2009).

Malicdan, M. C. V. et al., "Prophylactic treatment with sialic acid metabolites precludes the development of the myopathic phenotype in the DMRV-hIBM mouse model," Nature Medicine, 15(6):690-695 (2009).

Nishino, I. et al., "Distal myopathy with rimmed vacuoles is allelic to hereditary inclusion body myopathy," Neurology, 59:1689-1693 (2002).

Nishino, I. et al., "Muscular dystrophies," Current Opinion in Neurology, 15:539-544 (2002).

Noguchi, S. et al., "Reduction of UDP-N-acetylglucosamine 2-Epimerase/N-Acetylmannosamine Kinase Activity and Sialylation in Distal Myopathy with Rimmed Vacuoles," The Journal of Biological Chemistry, 279(12):11402-11407 (2004).

Oetke, C. et al., "Evidence for efficient uptake and incorporation of sialic acid by eukaryotic cells," European Journal of Biochemistry, 268(16):4553-4561 (2001).

Oetke, C. et al., "Versatile Biosynthetic Engineering of Sialic Acid in Living Cells Using Synthetic Sialic Acid Analogues," The Journal of Biological Chemistry, 277:6688-6695 (2002).

Penner, J. et al., "Influence of UDP-GlcNAc 2-Epimerase/ManNAc Kinase Mutant Proteins on Hereditary Inclusion Body Myopathy," Biochemistry, 45:2968-2977 (2006).

Pubchem Compound Database, CID 440962, "N-acetylneuraminate 9-phosphate," Created on Date: Jun. 24, 2005, 5 pages.

Ricci, E. et al., "NCAM is hyposialylated in hereditary inclusion body myopathy due to GNE mutations," Neurology, 66:755-758 (2006).

Rota, P. et al., "General and chemoselective N-transacylation of secondary amides by means of perfluorinated anhydrides," Angewandte Chemie International Edition, 49(10):1850-1853 (2010).

Seppala, R. et al., "Mutations in the Human UDP-N-Acetylglucosamine 2-Epimerase Gene Define the Disease Sialuria and the Allosteric Site of the Enzyme," Am. J. Hum. Genet., 64:1563-1569 (1999).

Sparks, S. E. et al., "Use of a cell-free system to determine UDP-N-acetylglucosamine 2-epimerase and N-acetylmannosamine kinase activities in human hereditary inclusion body myopathy," Glycobiology, 15(11):1102-1110 (2005).

Wajnrajch, M. P., "Physiological and Pathological Growth Hormone Secretion," Journal of Pediatric Endocrinology & Metabolism, 18(4):325-338 (2005).

International Preliminary Report on Patentability for International Application No. PCT/US2012/061737, dated Apr. 29, 2014, 9 pages.

International Preliminary Report on Patentability for International Application No. PCT/US2011/043910, dated Jan. 15, 2013, 8 pages.

International Preliminary Report on Patentability for International Application No. PCT/US2013/022167, dated Jul. 22, 2014, 4 pages.

Gavezzotti, A., "Are Crystal Structures Predictable?" Accounts of Chemical Research, 27(10):309-314, 1994.

Vippagunta, S. R. et al., "Crystalline Solids," Advanced Drug Delivery Reviews, 48:3-26, 2001.

Supplementary Partial European Search Report for European Application No. 12843460.2, mailed Feb. 25, 2015, 6 pages.

Dufner, G. et al., "Base- and Sugar-Modified Cytidine Monophosphate N-Acetylneuraminic Acid (CMP-Neu5Ac) Analogues—Synthesis and Studies with α(2-6)-Sialyltransferase from Rat Liver," European Journal of Organic Chemistry, 2000(8):1467-1482 (Apr. 2000).

Liu, J. L-C et al., "Overproduction of CMP-Sialic Acid Synthetase for Organic Synthesis," J. Am. Chem. Soc., 114(10):3901-3910 (1992).

Martin, R. et al., "The synthesis and enzymatic incorporation of sialic acid derivatives for use as tools to study the structure, activity, and inhibition of glycoproteins and other glycoconjugates," Bioorganic & Medicinal Chemistry, 6(8):1283-1292 (1998).

Nishino, I., "Development of a Fundamental Therapy for Distal Myopathy with Rimmed Vacuoles," Research Report Summary, Heisei 19 Soukatsu / Buntan Kenkyu Houkokusho, pp. 1-7 (2008) (with English Abstract).

Supplementary European Search Report for European Application No. 12843460.2, mailed Aug. 12, 2015, 14 pages.

Supplementary European Search Report for European Application No. 13739040.7, mailed Aug. 4, 2015, 8 pages.

Horn, E. J. et al., "Investigation into an efficient synthesis of 2,3-dehydro-N-acetyl neuraminic acid leads to three decarboxylated sialic acid dimers," Carbohydrate Research, 343(5):936-940 (2008).

Sato, S. et al., "Studies on sialic acids. XIV. Lactone derivatives of N-Acetylneuraminic acid," Chemical & Pharmaceutical Bulletin, 36(12):4678 (1988).

\* cited by examiner

Particle Size Distribution of Un-sieved Sialic Acid

Particle Size distribution Plot for Extended Release Sialic Acid, 250 Final Blends Dissolution Plot of Sialic Acid 250 and 325mg EXTENDED RELEASE Tablets by Direct Compression Dissolution Profile of Sialic Acid 325 and 500 mg EXTENDED RELEASE Tablets Uncoated Dissolution Profile of Sialic Acid 325mg and 500mg EXTENDED RELEASE Tablets
(Coated), Initial Stability

Dissolution Profile of ManNAc 325mg Tablets

ManNAc (325 mg Tabs)

Sample #: 1,2,3,4,5,6
Lots: 11216-062   ALJ684
Comments: ManNAc

Dissolution Profile

DissolutionConditions
Sample Volume: 900 mL
Apparatus: USP 1 (Baskets)
Dissolution Medium: 50 mM Phosphate, pH 6.8
Basket Speed: 100 rpm
Pull Volume: 10 mL (No replenishment)
Temperature: 37C

| Sample | Time (hours) Dissolved (%LC) | | | | | |
|---|---|---|---|---|---|---|
| | 2 | 4 | 6 | 8 | 12 | 24 |
| 1 | 32 | 51 | 66 | 77 | 89 | 95 |
| 2 | 32 | 52 | 68 | 78 | 90 | 97 |
| 3 | 33 | 53 | 68 | 79 | 90 | 95 |
| 4 | 33 | 52 | 67 | 78 | 91 | 97 |
| 5 | 31 | 51 | 66 | 76 | 87 | 94 |
| 6 | 32 | 51 | 66 | 76 | 87 | 94 |
| Mean | 32 | 52 | 67 | 77 | 89 | 95 |
| %RSD | 1.5 | 1.5 | 1.7 | 1.8 | 1.6 | 1.5 |

METHODS AND FORMULATIONS FOR TREATING SIALIC ACID DEFICIENCIES

CROSS-REFERENCE TO RELATED APPLICATIONS

This application is a continuation-in-part application of International Application No. PCT/US2011/043910, filed on Jul. 13, 2011 and entitled "Method and Formulations for Treating Sialic Acid Deficiencies", which claims the benefit of priority to U.S. Provisional Patent Application No. 61/363,995, filed on Jul. 13, 2010 and entitled "Method and Formulations for Treating Sialic Acid Deficiencies". The contents of these applications are herein incorporated by reference in their entireties for all purposes.

BACKGROUND

Sialic acid is a sugar with a net negative charge. It is often present on terminating branches of N-glycans, O-glycans, and glycosphingolipids (gangliosides), and occasionally capping side chains of GPI anchors. Sialic acid modification of cell surface molecules plays a role in many biological phenomena such as protein structure stability, regulation of cell adhesion, and signal transduction. Sialic acid deficiency disorders such as Hereditary Inclusion Body Myopathy (HIBM or HIBM type 2), Nonaka myopathy, and Distal Myopathy with Rimmed Vacuoles (DMRV) are clinical diseases resulting from a reduction in sialic acid production.

HIBM is a rare autosomal recessive neuromuscular disorder caused by a biosynthetic defect in the sialic acid synthesis pathway. Eisenberg et al., *Nat. Genet.* 29:83-87 (2001). The disease usually manifests between the ages of 20 to 40 such as foot drop and slowly progressive muscle weakness and atrophy. Patients may suffer difficulties walking with foot drop, gripping, use of hands, and swallowing. The disease is progressive; most afflicted individuals become incapacitated and wheelchair-confined within two to three decades. No treatments are available.

Studies of an Iranian-Jewish genetic isolate mapped the mutation associated with HIBM to chromosome 9p12-13. Argov et al., *Neurology* 60:1519-1523 (2003). The causative mutations were identified for HIBM in the gene GNE, which encodes the bifunctional enzyme UDP-N-acetylglucosamine-2-epimerase/N-acetylmannosamine kinase (GNE/MNK). Eisenberg et al., *Nat. Genet.* 29:83-87 (2001). DMRV is a Japanese variant, allelic to HIBM. Nishino et al., *Neurology* 59:1689-1693 (2002).

The biosynthesis steps and feedback regulation of GNE/MNK is depicted in FIG. 1. The production of sialic acid on glycoconjugates requires the conversion of N-acetylglucosamine (conjugated to its carrier nucleotide sugar UDP) to sialic acid. The sialic acid subsequently enters the nucleus where it is conjugated with its nucleotide sugar carrier CMP to make CMP-sialic acid, which is used as a donor sugar for glycosylation reactions in the cell. CMP-sialic acid is a known regulator of GNE/MNK activity. Jay et al., *Gene Reg. & Sys. Biol.* 3:181-190 (2009). Patients with HIBM have a deficiency in the production of sialic acid by the GNE/MNK enzyme, which is involved in the first two steps of this sequence. Nearly twenty GNE mutations have been reported in HIBM patients from different ethnic backgrounds with founder effects among the Iranian Jews and Japanese. Broccolini et al., *Hum. Mutat.* 23:632 (2004).

Because the production of sialic acid is the key reason the mutation causes the disease, replacing a metabolite after the genetic block in the pathway could, in theory, alleviate symptoms of a sialic acid deficiency. Jay et al., *Gene Reg. and Sys. Biology* 3:181-190 (2009). In practice, however, administering one or more compounds in the sialic acid biosynthetic pathway in vivo is a significant challenge. These compounds have extraordinarily rapid clearance rates and are excreted in the urine before they can be metabolized.

SUMMARY OF THE INVENTION

In one embodiment, the present invention provides an extended release pharmaceutical formulation comprising about 25% to about 50% w/w of a sialic acid, or a pharmaceutically acceptable salt, solvate, or ester thereof; about 20% to about 40% w/w of one or more water-swellable, pH independent polymers or one or more hydrogel-forming polymers; about 15% to about 30% w/w of one or more anionic, pH-dependent, gel-forming polymers; and about 3% to about 8% w/w of one or more hydrocolloid polymers or one or more cationic polymers.

In another embodiment, the present invention provides a method for treating a sialic acid deficiency in an individual in need thereof comprising administering an effective amount of a sialic acid, or a pharmaceutically acceptable salt, solvate, or ester thereof, in an extended release formulation of the present invention.

DETAILED DESCRIPTION

Figure 1:
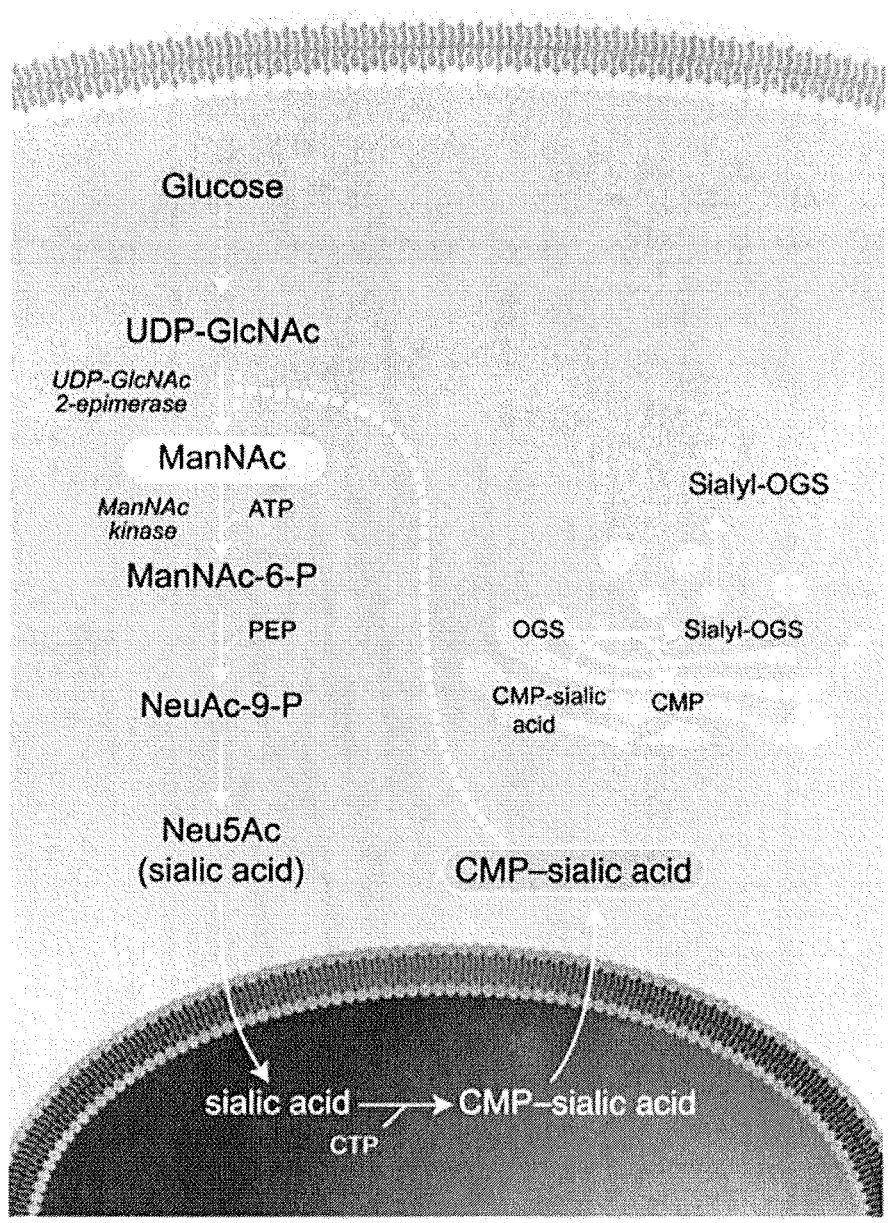
FIG. 1 is a diagram of intracellular sialic acid metabolism.

Extended release pharmaceutical formulations can comprise one or more compounds in the sialic acid biosynthetic pathway or derivative thereof and methods of treating and preventing sialic acid deficiencies utilizing the extended release pharmaceutical formulations. The one or more compounds in the sialic acid biosynthetic pathways can provide individuals with sialic acid deficiencies stable and steady day and nighttime sialic acid replacement, in the form of sialic acid, or other compounds in the sialic acid biosynthetic pathway or derivatives thereof, without high concentration spikes across a broad range of genotypes and in multiple tissues. This benefit can be achieved by use of one or more extended release formulations in combination with compounds in the sialic acid biosynthetic pathway or derivative thereof. The terms "extended release" and "sustained release" are used interchangeably throughout this application.

Extended release formulations can comprise an effective amount of one or more therapeutic agents; one or more pharmaceutically acceptable, water swellable, pH independent polymer; one or more pharmaceutically acceptable anionic, pH dependent polymer; and one or more polymers selected from the group consisting of one or more pharmaceutically acceptable cationic polymers and one or more pharmaceutically acceptable hydrocolloids. In such formulations, the one or more therapeutic agents can include therapeutic agents with various solubilities, such as soluble, partially soluble, sparingly soluble, or essentially insoluble therapeutic agents. The one or more therapeutic agents may also include therapeutic agents characterized as having hydrophobic or hydrophilic properties. Thus, the extended release formulations can accommodate, for example, a wide variety of one or more compounds in the sialic acid biosynthetic pathway, or sialic acid, or derivatives thereof, regardless of whether such one or more compounds have hydrophilic or hydrophobic properties, and regardless of the solubility of the one or more compounds.

It should be understood, however, that a wide variety of active agents, such as the non-limiting examples discussed below under the heading "Therapeutic Agent" can be included. An extended release formulation often includes an amount of an active agent, for example sialic acid or a pharmaceutically acceptable salt thereof, that is effective for treatment or prophylaxis of a sialic acid deficiencies, although this is not required unless otherwise specified.

DEFINITIONS

"Administration" includes all routes of administration, for example and without limitation, oral, parenteral, intervenous, inter-arterial, transdermal, transmucosal, etc. Unless otherwise specified, administration can be local or systemic. Administration can also include prescribing or filling a prescription for a drug or pharmaceutical formulation.

The terms "oral administration" and "oral ingestion" refer to oral delivery to an individual and that result in the deposition of the pharmaceutical formulation into the gastrointestinal tract (including the gastro portion of the gastrointestinal tract, i.e., the stomach) of the patient. Accordingly, oral administration and oral ingestion include, for example, ingestion of a solid or liquid pharmaceutical composition, oral gavage, and the like. Oral administration can also include prescribing or filling a prescription for a pharmaceutical formulation, such as a tablet, capsule, oral gavage, etc., that is designed for oral administration, or that includes instructions or directions for oral ingestion.

"Containing about" has its usual meaning in the art, except when it is used in connection with the amount of a pharmaceutically active agent, such as the therapeutic agents discussed below. When used in connection with a therapeutic agent, "containing about" refers to an amount of therapeutic agent that provides, at any given time after administration, between 80% and 125% of the whole blood, serum, or plasma concentration that is provided by the specified amount of pharmaceutically active agent, in the specified formulation or dosage form (if any) at the same time after administration. As an example, "containing about 250 mg sialic acid" means an amount of sialic acid that provides, at any given time after administration, between 80% and 125% of the whole blood, serum, or plasma concentration that is provided by 250 mg sialic acid at the same time after administration in the specified formulation or dosage form.

The terms "treating" and "treatment" include approaches for obtaining beneficial or desired results including clinical results. Beneficial or desired clinical results include, but are not limited to, one or more of the following: decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, increasing production of sialic acid, the sialylation precursor CMP-sialic acid (e.g., increasing intracellular production of sialic acid) and restoring the level of sialylation in muscle and other proteins, decreasing the dose of one or more other medications required to treat the disease, and/or increasing the quality of life. "Treating" a patient with a formulation described herein includes management of an individual to inhibit or cause regression of a disease or condition.

"Prophylaxis," "prophylactic treatment," or "preventive treatment" refer to prevention of the occurrence of symptoms and/or their underlying cause, for example, prevention of a disease or condition in an individual susceptible to developing a disease or condition, for example, individuals with genetic predisposition, current or previous exposure to relevant environmental factors, exposure to predisposing diseases or disorders, and the like. Prophylaxis and prevention are not limited to situations where the disease or condition does not occur in all instances, but include situations where the chance of being afflicted with a disease or condition is reduced.

"Delaying" the progression of a disease means to defer, hinder, slow, retard, stabilize, and/or postpone development of the disease. This delay can be of varying lengths of time, depending on the history of the disease and/or individual being treated.

"Effective amount" includes an amount of a pharmaceutical formulation including one or more compounds in the sialic acid biosynthetic pathway that provides the one or more compounds in the sialic acid biosynthetic pathway in a sufficient amount to render a desired treatment outcome. More than one dosage can be used to achieve an effective amount constituted within one or more doses. Thus, either a single dose or multiple doses can be administered to achieve the desired treatment endpoint.

A "therapeutically effective amount" refers to an amount of a pharmaceutical formulation including one or more compounds in the sialic acid biosynthetic pathway sufficient to produce a desired therapeutic outcome (e.g., reduction of severity of a disease or condition). A "prophylactically effective amount" refers to an amount of a pharmaceutical formulation including one or more compounds in the sialic acid biosynthetic pathway sufficient to prevent or reduce severity of a future disease or condition when administered to an individual who is susceptible and/or who can develop a disease or condition.

The term "individual" refers to an animal, for example, a mammal and includes, but is not limited to, human, bovine, horse, feline, canine, rodent, or primate. An individual is typically a human, although this is not required unless otherwise specified.

As used herein and in the appended claims, the singular forms "a," "or," and "the" include plural referents unless the context clearly dictates otherwise.

Extended Release Formulations

In one embodiment of the present invention, the extended release formulation comprises an effective amount of one or more therapeutic agents; one or more pharmaceutically acceptable, water swellable, pH independent polymer; one or more pharmaceutically acceptable anionic, pH dependent polymer; and one or more polymers selected from the group consisting of one or more pharmaceutically acceptable cationic polymers and one or more pharmaceutically acceptable hydrocolloids. In another embodiment of the present invention, the extended release formulation comprises an effective amount of one or more therapeutic agents; one or more pharmaceutically acceptable, hydrogel-forming polymers; one or more pharmaceutically acceptable anionic, pH dependent polymer; and one or more polymers selected from the group consisting of one or more pharmaceutically acceptable cationic polymers and one or more pharmaceutically acceptable hydrocolloids. Such extended release formulations can further comprise one or more additional components, such as one or more of a diluent, an excipient, an antioxidant, a lubricant, a colorant, a binder, a disintegrant, and the like. The extended release formulation can be one of the formulations described in U.S. Patent Application Publication No. 2010/0160363, published on Jun. 24, 2010, or U.S. Patent Application Publication No. 2010/0159001, published Jun. 24, 2010, which are incorporated herein by reference in their entireties, particularly for their description of formulations and polymers.

The one or more therapeutic agents can be one or more compounds in the sialic acid biosynthetic pathway or a derivative thereof or a pharmaceutically acceptable salt of the foregoing. Reference to and description of extended release pharmaceutical formulations comprising any one or more derivatives of compounds in the sialic acid biosynthetic pathway below includes extended release pharmaceutical formulations comprising any one or more derivatives, analogs, prodrugs, and/or unnatural precursor compounds in the sialic acid biosynthetic pathway.

Polymer

The extended release formulations can include one or more polymers. The one or more polymer can include one or more natural polymers, such as polysaccharides and proteins, modified natural polymers, or synthetic polymers. Examples of polymers include hydrophobic polymers, hydrophilic polymers, hydrogel-forming polymers, soluble polymers, insoluble polymers, biodegradable polymers, nonbiodegradable polymers, and mucoadhesive polymers.

The one or more polymers can include one or more hydrophobic polymers. Examples of hydrophobic polymers include polyethylene, polyvinyl chloride, ethyl cellulose or acrylate polymers and their copolymers.

The one or more polymers can include one or more hydrophilic polymer. Examples of hydrophilic polymers include a) cellulose derivatives such as methylcellulose (MC), hydroxyethyl-cellulose, hydroxypropylmethyl-cellulose (HPMC), or sodium carboxymethylcellulose, b) noncellulose natural or semisynthetic polymers such as agar-agar, carob gum, alginates, molasses, polysaccharides of mannose and galactose, or chitosan and modified starches and c) polymers of acrylic acid such as carbopol polymers.

The one or more polymers can include one or more hydrogel-forming polymers, which are often in the form of a hydrogel although this is not required unless otherwise specified. Examples of hydrogel-forming polymers include, but are not limited to, polyhydroxyethyle methylacrylate (PHEMA), polyvinyl alcohol (PVA), polyvinyl pyrrolidone (PVP), polyethylene oxide (PEO), and polyacrylamide (PA). The hydrogel-forming polymer can be polyethylene oxide, such as Polyox™ water soluble resin (Dow Chemical Company, Mich., USA).

The one or more polymers can include one or more soluble polymers. Examples of soluble polymers include, but are not limited to, polyethylene glycol (PEG), PVA, PVP, or HPMC.

The one or more polymers can include one or more biodegradable polymers. Examples of biodegradable polymers include, but are not limited to, polylactic acid (PLA), polyglycolic acid (PGA), poly(lactic/glycolic acid) (PLGA), polycaprolactone (PCL), polyanhydrides, or polyorthoesters. However, polylactide can be excluded from some formulations. Further, copolymers of polylactide, such as poly (lactide-co-glycolide), can be excluded from some formulations.

The one or more polymers can include one or more nonbiodegradable polymer. Examples of nonbiodegradable polymers include, but are not limited to, polyethylene vinyl acetate, polydimethyl siloxane (PDS), polyether urethane (PEU), polyvinyl chloride (PVC), cellulose acetate (CA), and ethyl cellulose (EC).

The polymer can include one or more mucoadhesive polymers. Examples of mucoadhesive polymers include, but are not limited to, polycarbophil, sodium carboxymethyl cellulose, polyacrylic acid, tragacanth, methyl cellulose, pectin, natural gums, xanthan gum, guar gum, or karaya gum.

The one or more polymers can be exactly one polymer. When the one or more polymers are more than one polymer, they can include, as a non-limiting example exactly two polymers, exactly three polymers, exactly four polymers, exactly five polymers, etc.

Thus, an extended release formulation with one or more polymers can comprise: (i) one or more hydrocolloid polymer; (ii) one or more an anionic, pH-dependent, gel forming polymers, and (iii) either one or more water-swellable, pH independent polymers or one or more hydrogel-forming polymer. The weight percent ratio of polymers (i):(ii):(iii) can be about 1:5:5 or about 1:5:6.

The one or more polymers can include a combination of one or more pharmaceutically acceptable, water swellable, pH independent polymers; one or more pharmaceutically acceptable, anionic, pH dependent polymers; and one or more pharmaceutically acceptable polymers selected from the group consisting of cationic polymers and hydrocolloids. The one or more polymers can be present in a matrix that also contains other materials, for example, one or more therapeutic agents such as the one or more therapeutic agents described below. The matrix can also contain one or more of the additional formulation components described below, although this is not required unless otherwise specified.

Examples of water-swellable, pH independent polymers include, but are not limited to, carbohydrate-based polymers such as, for example, hypromellose (formerly known as the family of hydroxypropyl methylcellulose), hydroxypropyl ethyl celluloses, hydroxypropyl cellulose, hydroxyethyl cellulose, methyl cellulose or other constituents Grades of hypromellose polymers include one or more of the E and K series, such as for example, Dow Chemical Company's (Midland, Mich. USA) or Aqualon's (with a North American presence in Wilmington, Del.) E4M, E10M, K100LV, K4M, K15M, K25M, K100M, K200M. Grades of hydroxyethyl cellulose include one or more of Aqualon's Natrasol polymers MIX (weight average mol. wt. 1,300,000), HX (weight average mol. wt. 1,000,000), H (weight average mol. wt. 1,000,000), M (weight average mol. wt. 720,000) and G (weight average mol. wt. 1,150,000). Grades of hydroxypropyl cellulose include one or more of Aqualon's HPC polymers MF and MXF (weight average mol. wt. 580,000) and KF and FIXF (weight average mol. wt. 1,150,000). Grades and ethyl cellulose include one or more of Dow Chemical Company's Ethocel polymers 7FP, 10FP and 100FP and Aqualon's polymers T10EC, N7, N10, N17, N22, N50, N100 and N200. Hypromellose (e.g., hypromellose Type 2208) and Methocel® (e.g., Methocel® K100MPremium CR, Colorcon) can be used, although neither is required unless otherwise specified.

Examples of hydrogel-forming polymers include poly(ethylene glycol), polyethylene oxide (e.g. Polyox WSR), and the like.

Anionic, pH-dependent polymers can be anionic, pH dependent gel-forming polymers, such as alginate salts such as sodium, potassium or ammonium alginate salts, or combinations thereof, carboxymethyl cellulose, such as sodium carboxylmethyl cellulose and the like, or mixtures of one or more alginate salts and carboxymethyl cellulose and the like. Sodium alginate (e.g., Protanal®, FMC BioPolymer) can be used, although it is not required unless otherwise specified.

Examples of cationic polymers include chitosan, derivatives of chitosan such as trimethylchitosan and quartermised chitosan, and chitosan-derived materials such as those taught in U.S. Pat. No. 5,747,475, which is hereby incorporated by reference in its entirety. When chitosan or a derivative of chitosan is used, it can be either high or low molecular weight, unless one is specified.

The hydrocolloid polymer is often one or more carrageenan, although this is not required unless otherwise specified. Carrageenans include iota, kappa, and lambda carrageenans. Salt forms of carrageenans, such as sodium carrageenan, can be used. Grades of iota carrageenan include carrageenan NF, AEP brand colloids (Hadley, N.Y. USA) FD433 (1% viscosity; 300-400 cps) and FD384 (1% viscosity; about 100 cps). The viscosity of other carrageenan products ranges from about 50 to about 4000 cps, or about 1500-2000 cPs, or about 1600 cPs. These viscosities are measured according to methods well known to one skilled in the art, such as the industrial standard methods used by the manufacturers including FMC Corp.

Additional Formulation Components

Extended release pharmaceutical formulations can comprise one or more diluents, one or more excipients, one or more antioxidants, one or more lubricants, one or more colorants, one or more binders, one or more disintegrants, and the like.

Diluents can be selected so as not to affect the biological activity of the combination. Examples of such diluents include distilled water, buffered water, physiological saline, PBS, Ringer's solution, dextrose solution, and Hank's solution.

Examples of excipients include of lactose, microcrystalline cellulose, corn starch, potato starch, wheat starch, sucrose, D-mannitol, precipitated calcium carbonate, dextrin, pre-gelatinized starch, and combinations thereof. When one or more excipients are used, they can be present in an amount of about 10 to about 90 parts by weight based on the total weight of the formulation, for example, from about 40% to about 50%, about 50% to about 60%, about 60% to about 70%, or about 50% to about 70% w/w. As an example, the one or more excipients can be microcrystalline cellulose. As another example, the one or more excipients can be a mixture of microcrystalline cellulose and colloidal silicon dioxide (e.g., ProSolv® SMCC HD90). When microcrystalline cellulose and colloidal silicon dioxide are used together, the combination of microcrystalline cellulose and colloidal silicon dioxide can be about from 1% to about 10% w/w of the formulation, or about 5% w/w of the formulation.

The one or more excipients can include one or more pH adjusting agents, buffering agents, toxicity adjusting agents, wetting agents, detergents, or stabilizing agents. Examples of such materials can be found in Remington: The Science and Practice of Pharmacy, 20th Edition. Baltimore, Md.: Lippincott Williams & Wilkins, 2000, which is hereby incorporated by reference in its entirety.

When one or more binders are used, they can include one or more of hydroxypropylcellulose, direct tableted microcrystalline cellulose, HPMC, MC, hydroxyethylcellulose, hydroxymethylcellulose, carboxymethyl cellulose, PVP, PVA, paste, arabic gum, dextrin, gelatin, and alginates, and can be present in an amount of about 2% to about 60% w/w.

When one or more disintegrants are used, they can include one or more of sodium starch glycolate, crosspovidone, cross carmellose sodium, low-substituted hydroxypropylcellulose, starch, carboxymethylcellulose calcium, calcium carbonate, and sodium bicarbonate, and can be present in an amount from about 0.1% to about 32% w/w.

When one or more lubricants are used, they can include one or more of magnesium stearate, calcium stearate, talc, light anhydrous silicic acid, and polyethyl glycols, and can constitute about 0.1% to about 20% w/w. Although not required unless otherwise specified, magnesium stearate is a commonly used lubricant. Extended release formulations can comprise about 0.1% to about 1%, or about 0.5% w/w magnesium stearate.

When a colorant is used, it can include one or more of titanium dioxide, iron oxide, magnesium carbonate, calcium sulfate, magnesium oxide, magnesium hydroxide, aluminum lakes, for example, Blue No. 1 Aluminum Lake, Red No. 40 Aluminum Lake, and the like.

These one or more additional formulation components, along with the one or more polymers and a therapeutic agent, can be in the form of a matrix. For example, the matrix can include, on a w/w basis, a combination of about 10% to about 90%, or about 20% to about 50%, or about 30% to about 40% of one or more pH independent polymers; and about 10% to about 90%, or about 10% to about 50%, or about 10% to about 30%, or about 15% to about 25% of one or more anionic, pH dependent polymers, such as pH dependent gel-forming polymers; and about 0.1% to about 25%, or about 0.5% to about 20%, or about 5% to about 15% of one or more cationic polymers and/or hydrocolloids.

Such formulations can provide extended release of a wide variety of drugs. For example, when a highly water soluble drug is used, its release rate can be extended by one or more of the following modifications: using a lower drug substance load and increased total polymer content; using low-water soluble polymers, such as ethyl cellulose, as the pH-independent water swellable polymer; using high molecular weight polymers; avoiding or minimizing the use of water soluble diluents using low diluent loading; using less of the hydrocolloid (e.g., carageenen or chitosan); and, in tablet formulations, reducing the surface area of the tablet relative to its volume, for example, by using a round tablet.

Poorly soluble drugs can also be accommodated in such formulations. For example, when a poorly water soluble drug is used, one or more of the following modifications can provide an acceptable release rate: use a composition where the total amount of all polymers is about 20% to about 30%; use a water soluble diluent, for example, lactose; minimize or avoid the use of water-insoluble polymers such as ethyl cellulose and replace such polymers with low-molecular weight polymers with greater water solubility, such as hypromellose and hydroxypropyl cellulose; include a surfactant or solubilizer as an excipient; micronize the drug; and maximize the surface area to volume ratio of the formulation, for example, by using a multi-particulate minicab system.

Therapeutic Agent

Compounds that can be administered as a therapeutic agent to an individual who has or is suspected of having a sialic acid deficiency disorder include one or more of sialic acid, compounds in the sialic acid biosynthetic pathway, derivatives thereof, and pharmaceutically acceptable salts of any of the foregoing. These one or more compounds can act as substrate replacements for compounds in the sialic acid biosynthetic pathway. The one or more of sialic acid, compounds in the sialic acid biosynthetic pathway, derivatives thereof, and pharmaceutically acceptable salts of any of the foregoing can be sialic acid or a pharmaceutically acceptable salt thereof. Thus, any of the extended release formulations described herein, including without limitation those discussed above, can comprise an effective amount of one or more of the therapeutic agents mentioned in this section, such as an effective amount of sialic acid or a pharmaceutically acceptable salt thereof.

One or more compounds in the sialic acid biosynthetic pathway or a derivative thereof can be one or more compounds or pharmaceutically acceptable salt thereof, that are at or downstream from ManNAc in the sialic acid biosynthetic pathway. The sialic acid biosynthetic pathway, including several compounds at or downstream from ManNAc, are depicted in FIG. 1. Examples of such compounds include ManAc-6-P, NeuAc-9-P, and Neu5Ac. Neu5Ac is also known as sialic acid.

One or more compounds in the sialic acid biosynthetic pathway or a derivative thereof can also be compounds or a pharmaceutically acceptable salt thereof, that are at or upstream from CMP-sialic acid in the sialic acid biosynthetic pathway. Several examples of such compounds are depicted in FIG. 1. As an example, the one or more compound in the sialic acid biosynthetic pathway or a derivative thereof can exclude glucose and pharmaceutically acceptable salts thereof.

One or more compounds in the sialic acid biosynthetic pathway or derivatives thereof can include one or more of mannosamine, N-acetyl mannosamine (ManNAc), ManNac-6-phosphate (ManNAc-6-P), UDP-GlcNAc, N-acetyl-neuraminic acid (NeuAc), NeuAc-9-phosphate (NeuAc-9-P), sialic acid (i.e., 5-N-acetylneuraminic acid), CMP-sialic acid, derivatives thereof, and pharmaceutically acceptable salts of the foregoing.

The one or more compounds in the sialic acid biosynthetic pathway or derivative thereof can include one or more of include N-acetylneuraminic acid (NeuAc) or a derivative thereof. Structures of such NeuAc or derivatives thereof include, but are not limited to, those defined by the formula below:

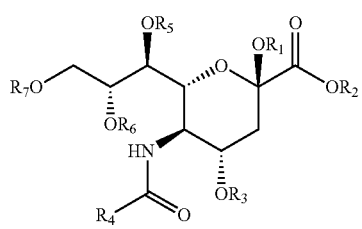

wherein each $R_1$, $R_2$, $R_3$, $R_5$, $R_6$, or $R_7$ is independently hydrogen, lower alkanoyl, carboxylate or lower alkyl; and $R_4$ is lower alkyl, lower alkanoylalkyl or lower alkyl alkanoyloxy.

Structures of ManNAc and derivatives thereof include, but are not limited to, those defined by the formula below:

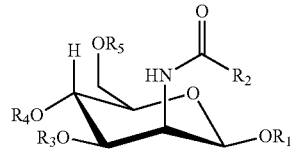

Wherein each $R_1$, $R_3$, $R_4$, or $R_5$ is independently hydrogen, lower alkanoyl, carboxylate or lower alkyl; and $R_2$ is lower alkyl, lower alkanoylalkyl or lower alkyl alkanoyloxy.

The term lower alkyl refers to $(C_1-C_6)$alkyl. A lower alkyl includes methyl, ethyl, propyl, isopropyl, butyl, iso-butyl, sec-butyl, pentyl, 3-pentyl, hexyl as well as $(C_3-C_6)$cycloalkyl moieties (e.g., cyclopropyl, cyclobutyl, cyclopentyl, or cyclohexyl), $(C_3-C_6)$cycloalkyl$(C_1-C_6)$alkyl (e.g., cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl), $(C_1-C_6)$alkoxy (e.g., methoxy, ethoxy, propoxy, isopropoxy, butoxy, iso-butoxy, sec-butoxy, pentoxy, 3-pentoxy, or hexyloxy) $(C_2-C_6)$alkenyl (e.g., vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl), $(C_2-C_6)$alkynyl (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl), $(C_1-C_6)$alkanoyl (e.g., acetyl, propanoyl or butanoyl), halo$(C_1-C_6)$alkyl (e.g., iodomethyl, bromomethyl, chloromethyl, fluoromethyl, trifluoromethyl, 2-chloroethyl, 2-fluoroethyl, 2,2,2-trifluoroethyl, or pentafluoroethyl), hydroxy$(C_1-C_6)$alkyl (e.g., hydroxymethyl, 1-hydroxyethyl, 2-hydroxyethyl, 1-hydroxypropyl, 2-hydroxypropyl, 3-hydroxypropyl, 1-hydroxy butyl, 4-hydroxybutyl, 1-hydroxypentyl, 5-hydroxypentyl, 1-hydroxyhexyl, or 6-hydroxyhexyl), $(C_1-C_6)$alkoxycarbonyl (e.g., methoxycarbonyl, ethoxycarbonyl, propoxycarbonyl, isopropoxycarbonyl, butoxycarbonyl, pentoxycarbonyl, or hexyloxycarbonyl), $(C_1-C_6)$alkylthio (e.g., methylthio, ethylthio, propylthio, isopropylthio, butylthio, isobutylthio, pentylthio, or hexylthio), and/or $(C_2-C_6)$alkanoyloxy (e.g., acetoxy, propanoyloxy, butanoyloxy, isobutanoyloxy, pentanoyloxy, or hexanoyloxy).

In one non-limiting example, $R_2$ is methyl, and each of $R_1$, $R_3$, $R_4$, and $R_5$ is hydrogen. In another non-limiting example the ManNAc or derivative thereof is N-acetyl mannosamine (ManNAc). In yet another non-limiting example, the ManNAc or derivative thereof is N-levulinoylmannosamine (ManLev) or N-azidoacetylmannosamine (ManNAz).

The one or more compounds in the sialic acid biosynthetic pathway or derivative thereof can be an ester of a compound in the sialic acid biosynthetic pathway. As an example, the one or more compounds in the sialic acid biosynthetic pathway or derivative thereof can be an ester of sialic acid or MaNAc, such as an ester of sialic acid. The one or more compounds in the sialic acid biosynthetic pathway or derivative thereof can also be prodrug of sialic acid. WO 2010/131712, published Nov. 18, 2010, which is hereby incorporated by reference in its entirety, describes derivatives of compounds in the sialic acid biosynthetic pathway that can be used.

The one or more compounds in the sialic acid biosynthetic pathway or derivatives thereof can include sialic acid or a derivative thereof. The sialic acid or derivative thereof can be sialic acid. The sialic acid or derivative thereof can also be a sialic acid analog such as N-levulinoyl sialic acid (SiaLev) or N-azidoacetyl sialic acid (SiaNAz). The sialic acid can be bound as a glycoconjugate. The sialic acid or derivative thereof can be an unnatural precursor, such as, for example, sialylactose.

An extended release formulation can comprise about any of one, two, three, or four compounds in the sialic acid biosynthetic pathway or a derivative thereof for example, two compounds in the sialic acid biosynthetic pathway or a derivative thereof. Therefore, for example, the extended release formulation can include ManNAc or a derivative thereof and sialic acid or a derivative thereof, or ManNAc and sialic acid.

The amount of one or more compounds in the sialic acid biosynthetic pathway or derivative thereof in the extended release formulation can be an amount effective for treatment or prophylaxis of one or more conditions associated with sialic acid deficiencies, such as the conditions discussed above, for example, by increasing sialic acid production and/or increasing sialylation.

The ratio of the two or more compounds in the sialic acid biosynthetic pathway or derivative thereof, can minimize feedback inhibition of the sialic acid biosynthetic pathway, allow efficient delivery of the two or more compounds in the sialic acid biosynthetic pathway or derivative thereof to muscle cells, or both. The two or more compounds in the sialic acid biosynthetic pathway or derivative there of can be ManNAc or a derivative thereof and sialic acid or a derivative thereof, such as ManNAc and sialic acid.

For example, the two compounds in the sialic acid pathway or derivatives thereof can be present in a weight to weight percentage ratio of at least one of about 5% to about 95%: about 95% to about 5%, about 5% to about 50%:about 95% to about 50%, and about 10% to about 40%:about 90% to about 60%. They can also be present in a weight to weight percentage ratio of at least one of about 90%:10%, about 80%:20%, about 70%:30%, about 60%:40%, about 50%:50%, about 40%:60%, about 30%:70%, about 20%:80%, and about 10%:90%, for example, about 50%:50%.

Exemplary Formulations

The extended release formulation can comprise a water-swellable, pH independent polymer (e.g., hypromellose). The extended release formulation can further comprise an anionic, pH-dependent, gel-forming copolymer (e.g., an alginate salt). The extended release formulation can further comprise a hydrocolloid polymer (e.g., carrageenan). The extended release formulation can comprise a water-swellable, pH independent polymer (e.g. hypromellose), an anionic, pH-dependent, gel-forming polymer (e.g., an alginate salt), and a hydrocolloid polymer (e.g., a carrageenan). The extended release formulation can comprise hypromellose (e.g. hypromellose Type 2208 or Methocel K100M), sodium alginate (e.g. Protanal), and a lambda carrageenan (e.g. Viscarin GP-209). These polymers can be used in conjunction with any of the one or more therapeutic agents discussed above.

As an example, an extended release formulation can comprise sialic acid, or a pharmaceutically acceptable salt thereof, as the therapeutic agent; one or more hydrocolloid polymers; one or more anionic, pH-dependent gel forming polymers; one or more water swellable, pH independent polymers; and optionally one or more lubricant and/or an excipient. As another example, an extended release formulation can comprise sialic acid, or a pharmaceutically acceptable salt thereof, carrageenan, sodium alginate, and either hypromellose or polyethylene oxide. As yet another example, the extended release formulation can comprise sialic acid, or a pharmaceutically acceptable salt thereof, carrageenan, sodium alginate, either hypromellose or polyethylene oxide, magnesium strearate, microcrystalline collulose, and colloidal silicon dioxide.

Other examples of extended release formulations comprise one or more hydrogel-forming polymers (e.g., a polyethylene oxide). Such extended release formulations can further comprise one or more anionic, pH-dependent, gel-forming polymers (e.g. alginate salts), and can further comprise one or more hydrocolloids (e.g., carrageenan).

As an example, an extended release formulation can comprise one or more hydrogel-forming polymer such as polyethylene oxide, one or more anionic, pH-dependent, gel-forming copolymers such as alginate salts, for example, sodium alginate, and one or more hydrocolloid polymers such as carrageenan, for example lambda carrageenan.

In general, the one or more compounds in the sialic acid pathway or derivatives thereof can be from about 0.1 to about 99.9% by weight of an extended release formulation. For example, the one or more compounds in the sialic acid pathway or derivatives thereof can be present in an extended release formulation from about 20% to about 30%, about 30% to about 40%, about 40% to about 50%, or about 20% to about 50%. The one or more polymers can be present from about 40% to about 50%, about 50% to about 60%, about 60% to about 70%, or about 50% to about 70% by weight of the extended release formulation. Thus, the one or more polymers can be present in an extended release formulation in an amount ranging from 5 to 40 parts by weight, or from 10 to 20 parts by weight, relative to 100 parts by weight of the one or more compounds in the sialic acid pathway or derivatives thereof. Exemplary extended release formulations include those listed in Table A, where any of the listed therapeutic agents can be used in combination with at least one of any of polymers 1, 2, 3A or 3B the same as if each and every combination of therapeutic agent and polymer or combination of polymers were specifically and individually listed. Extended release formulations can comprise a therapeutic agent of Table A and any one or more of a polymer selected from Polymers 1, 2 and 3 (A and/or B) of Table A, for example, a therapeutic agent of Table A, a polymer 1 of Table A, a polymer 2 of Table A, and either a polymer 3A of Table A or a polymer 3B of Table A, just as if each and every combination of therapeutic agent and polymer combination were specifically and individually listed. One specific example of an extended release formulation comprises sialic acid, carrageenan (e.g., a lambda carrageenan such as Viscarin GP-209), an alginate salt (e.g., sodium alginate such as Protanal® LF 120M), and either (i) hypromellose (e.g., hypromellose Type 2208) or (ii) polyethylene oxide (e.g., Polyox), or a pharmaceutically acceptable salt of any of the foregoing.

TABLE A

Exemplary Components for use in Extended Realease Formulations.

| Formulation Component | Weight Percent of Component in Formulation |
|---|---|
| Therapeutic Agent (A compound in the sialic acid biosynthetic pathway or derivative thereof or salt | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof |

TABLE A-continued

Exemplary Components for use in Extended Realease Formulations.

| Formulation Component | Weight Percent of Component in Formulation |
|---|---|
| of any of the foregoing) | or pharmaceutically acceptable salts of the foregoing. |
| Polymer 1 (Hydrocolloid Polymer) | Carrageenan (e.g., iota, kappa or lambda carrageenan, or a salt thereof, such as Viscarin GP-209, FMC BioPolymer) |
| Polymer 2 (Anionic, pH-dependent, gel forming polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. |
| Polymer 3B (Hydrogel-forming polymer) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). |

Extended release formulations that comprises a therapeutic agent of Table A, a polymer 1 of Table A, a polymer 2 of Table A and either a polymer 3A or a polymer 3B of Table A, can comprise one or more of the therapeutic agent and polymers in any of the weight percent ranges depicted in Table B.

TABLE B

Exemplary Weight Percent of Certain Components for Use in Extended Release Formulations.

| Formulation Component | Weight Percent of Component in Formulation |
|---|---|
| Therapeutic Agent (A compound in the sialic acid biosynthetic pathway or derivative thereof or salt of any of the foregoing) | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from about 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Polymer 1 (Hydrocolloid Polymer) | From about 1 to about 10; from about 1 to about 5; from about 3 to about 8; from about 4 to about 6; about any of 1, 2, 3, 4, 5, 6, 7, 8, 9 and 10. |
| Polymer 2 (Anionic, pH-dependent, gel forming polymer) | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Polymer 3A. (Water-swellable, pH independent polymer) Or Polymer 3B. (Hydrogel-forming polymer) | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |

An extended release formulation can further comprise one or more excipients, such as any of the one or more excipients described above. As an example, the one or more excipients can be microcrystalline cellulose or a combination of microcrystalline cellulose and colloidal silicon dioxide. When one or more excipients, such as microcrystalline cellulose and colloidal silicon dioxide, are present, they can be present in about 1 to about 20 or about 1 to about 15 or about 1 to about 10 or about 1 to about 5 or about 5 to about 20 or about 5 to about 15 or about 5 to about 10 or about 1, about 2, about 3, about 4, about 5, about 6, about 7, about 8, about 9 or about 10 weight percent.

An extended release formulation can further comprise one or more lubricants. When one or more lubricants are used, they can comprise a stearate salt, such as magnesium stearate. The one or more lubricants (e.g., a stearate salt such as magnesium stearate) can comprise be present in about 0.1 to about 2, about 0.1 to about 1.5, about 0.1 to about 1.0, about 0.1 to about 0.9, about 0.1 to about 0.8, about 0.1 to about 0.7, about 0.1 to about 0.6, about 0.1 to about 0.5, about 0.2 to about 0.8, about 0.3 to about 0.7, about 0.4 to about 0.6, about 0.1, about 0.2, about 0.3, about 0.4, about 0.5, about 0.6, about 0.7, about 0.8, about 0.9 or about 1.0 weight percent.

An extended release formulation can comprise both one or more excipients and one or more lubricant. When both one or more excipients and one or more lubricants are included, the one or more excipients, such as microcrystalline cellulose and colloidal silicon dioxide, can be present in about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent and the one or more lubricants, such as stearate salts like magnesium stearate, can be present in from about 0.1 to about 2 or about 0.1 to about 1.5 or about 0.1 to about 1.0 or about 0.01 to about 0.09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about 0.1, about 0.2, about 0.3, about 0.4, about 0.5, about 0.6, about 0.7, about 0.8, about 0.9 or about 1.0 weight percent. The one or more excipients and one or more lubricants can be present in a ratio of about any of 1:10 or 1:11 or 1:9 or 1:10.5 by weight.

Particular extended release formulations include those listed in Table C, where the compositions comprise a therapeutic agent, a polymer 1, a polymer 2, either a polymer 3A or a polymer 3B, an excipient and a lubricant, and it is understood that each and every combination of such components is intended the same as if each and every combination were specifically and individually listed.

TABLE C

Exemplary Extended Release Formulation Compositions.

| Formulation Component | Exemplary Specific Components |
|---|---|
| Therapeutic Agent (A compound in the sialic acid biosynthetic pathway or derivative thereof or salt of any of the foregoing) | mannosamine, N-acetyl mannosamine (ManNAc), ManNac-6-phosphate (ManNAc-6-P), UDP-GlcNAc, N-acetylneuraminic acid (NeuAc), NeuAc-9-phosphate (NeuAc-9-P), sialic acid (i.e., 5-N-acetylneuraminic acid), CMP-sialic acid, and/or derivatives thereof or pharmaceutically acceptable salts of the foregoing. |
| Polymer 1 (Hydrocolloid Polymer) | Carrageenan (e.g., iota, kappa or lambda carrageenan, or a salt thereof, such as Viscarin GP-209, FMC BioPolymer) |
| Polymer 2 (Anionic, pH-dependent, gel forming polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. |
| Polymer 3B (Hydrogel-forming polymer) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). |
| Excipient | lactose, microcrystalline cellulose, corn starch, potato starch, wheat starch, sucrose, D-mannitol, precipitated calcium carbonate, dextrin, pre-gelatinized starch, microcrystalline cellulose and colloidal silicon dioxide (e.g., ProSolv ® SMCC HD90) and combinations thereof. |
| Lubricant | Stearate salt (such as magnesium stearate (e.g., HyQual ®) and calcium stearate), talc, light anhydrous silicic acid, and solid polyethyl glycols and combinations thereof. |

Extended release formulations can be compositions described in Table C comprising the formulation components in any one of the weight percent ranges depicted in Table D. Each and every combination of such components and weight percentages is intended, just as if each and every combination of component and weight percentage were specifically and individually listed.

TABLE D

Exemplary Weight Percent of Certain Components for Use in Extended Release Formulations

| Formulation Component | Exemplary Specific Components | Exemplary w/w % |
|---|---|---|
| Therapeutic Agent (A compound in the sialic | mannosamine, N-acetyl mannosamine (ManNAc), ManNac-6-phosphate (ManNAc-6-P), UDP-GlcNAc, N-acetylneuraminic acid (NeuAc), NeuAc-9- | From about 20 to about 80; from about 20 to about 60; from about 20 to about 50; from about 20 to about 40; from about 20 to about |

TABLE D-continued

Exemplary Weight Percent of Certain Components for Use in Extended Release Formulations

| Formulation Component | Exemplary Specific Components | Exemplary w/w % |
|---|---|---|
| acid biosynthetic pathway or derivative thereof or salt of any of the foregoing) | phosphate (NeuAc-9-P), sialic acid (i.e., 5-N-acetylneuraminic acid), CMP-sialic acid, and/or derivatives thereof or pharmaceutically acceptable salts of the foregoing. | 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Polymer 1 (Hydrocolloid Polymer) | Carrageenan (e.g., iota, kappa or lambda carrageenan, or a salt thereof, such as Viscarin GP-209, FMC BioPolymer) | From about 1 to about 10; from about 1 to about 5; from about 3 to about 8; from about 4 to about 6; about any of 1, 2, 3, 4, 5, 6, 7, 8, 9 and 10. |
| Polymer 2 (Anionic, pH-dependent, gel forming co-polymer) | Alginate or salt thereof (e.g., sodium, potassium or ammonium alginate salt such as Protanal ®, FMC BioPolymer), carboxymethyl cellulose or salt thereof (e.g., sodium carboxymethyl cellulose). | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Polymer 3A (Water-swellable, pH independent polymer) | Hypromellose (e.g., hypromellose Type 2208, E and K series such as for example, Dow Chemical Company's (Midland, Mich. USA) or Aqualon's (with a North American presence in Wilmington, Del.) E4M, E10M, K100LV, K4M, K15M, K25M, K100M, K200M and mixtures of various molecular weights and grades); hydroxypropyl ethyl cellulose (Ethocel polymers 7FP, 10FP and 100FP and Aqualon's polymers T10EC, N7, N10, N17, N22, N50, N100 and N200, and mixtures thereof), hydroxypropyl cellulose (Aqualon's HPC polymers MF and MXF (mol. wt. 580,000) and KF and HXF (mol. wt. 1,150,000), and mixtures thereof); hydroxyethyl cellulose (e.g., Aqualon's Natrasol polymers HHX (mol. Wt. 1,300,000), HX (mol. wt. 1,000,000), H (mol. wt. 1,000,000), M (mol. wt. 720,000 and G (mol. wt. 1,150,000), and mixtures thereof); methyl cellulose.. | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |
| Polymer 3B (Hydrogel-forming polymer) | Polyhydroxyethyle methylacrylate (PHEMA), polyvinyl alcohol (PVA), polyvinyl pyrrolidone (PVP), polyethylene oxide (PEO), polyacrylamide (PA), polyethylene oxide (e.g., Polyox ™ water soluble resin, Dow Chemical Company, Mich., USA). | From about 20 to about 30; from about 20 to about 25; from about 25 to about 30; from about 22 to about 27; about any of 20, 21, 22, 23, 24, 25, 26, 27, 28, 29 and 30. |
| Excipient | lactose, microcrystalline cellulose, corn starch, potato starch, wheat starch, sucrose, D-mannitol, precipitated calcium carbonate, dextrin, pre-gelatinized starch, microcrystalline cellulose and colloidal silicon dioxide (e.g., ProSolv ® SMCC HD90) and combinations thereof. | From about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. |

TABLE D-continued

Exemplary Weight Percent of Certain Components for Use in Extended Release Formulations

| Formulation Component | Exemplary Specific Components | Exemplary w/w % |
|---|---|---|
| Lubricant | Stearate salt (such as magnesium stearate (e.g., HyQual ®) and calcium stearate), talc, light anhydrous silicic acid, and solid polyethyl glycols and combinations thereof. | From about 0.1 to about 2 or about 0.1 to about 1.5 or about 0.1 to about 1.0 or about .01 to about .09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. |

An exemplary and non-limiting weight percent ratios of Lubricant:Polymer 1:Excipient:Polymer 2:Polymer 3A or 3B:Therapeutic Agent can be about 1:8:10:40:50:85 or about 1:8.5:10.5:42.5:51:86.5 or about 1:8.4:10.6:42.4:51:86.6.

Exemplary extended release formulations of sialic acid are provided in Table E. Importantly ManNAc can be used in place or in combination with sialic acid in the formulations of Table E, just as if each of such formulations had been individually and specifically identified.

The loading of the one or more compounds in the sialic acid pathway or derivatives thereof in an extended release formulation can be about 20% to about 80% w/w, about 20% to about 60% w/w, about 20% to about 50% w/w, about 20% to about 40% w/w, about 15% to about 60% w/w, about 15% to about 50% w/w, about 15% to about 40% w/w, about 25% to about 60% w/w, about 25% to about 50% w/w, about 25% to about 40% w/w, about 30% to about 60% w/w, about 30% to about 50% w/w, about 30% to about 45% w/w, about 35% to

TABLE E

Exemplary Extended Release Formulations of sialic acid.

| Formulation Component | Exemplary w/w % |
|---|---|
| Sialic acid, or pharmaceutically acceptable salt thereof | From about 20 to about 80; from about 20 to about 60; from about 20 to about 50; from about 20 to about 40; from about 20 to about 30; from about 15 to about 60; from about 15 to about 50; from about 15 to about 40; from about 25 to about 60; from about 25 to about 50; from 25 to about 40; from about 25 to about 30; from about 30 to about 60; from about 30 to about 50; from about 30 to about 45; from about 30 to about 40; from about 35 to about 60; from about 35 to about 50; from about 35 to about 45; from about 40 to about 45; about any of 35, 36, 37, 38, 39, 40, 41, 42, 43, 44, 45, 46, 47, 48, 49 and 50. |
| Carrageenan (e.g., lambda carrageenan such as Viscarin GP-209, FMC BioPolymer) | From about 1 to about 10; from about 1 to about 5; from about 3 to about 8; from about 4 to about 6; about any of 1, 2, 3, 4, 5, 6, 7, 8, 9 and 10. |
| Alginate or a salt thereof (e.g., sodium, potassium or ammonium alginate salt such as Protanal ® LF 120M) | From about 15 to about 30; from about 15 to about 25; from about 15 to about 20; from about 20 to about 30; from about 20 to about 25; from about 2o to about 23; about any of 15, 16, 17, 18, 19, 20, 21, 22, 23, 24 and 25. |
| Hypromellose (such as hypromellose Type 2208, e.g., Methocel ® K100 M Premium CR) | From about 20 to about 50; from about 20 to about 40, from about 20 to about 30; from about 20 to about 25; from about 25 to about 30; from about 22 to about 27; about any of 20, 21, 22, 23, 24, 25, 26, 27, 28, 29 and 30. |
| Polyethylene oxide (such as Polyethylene Oxide WSR, e.g., Polyox ™ water soluble resin, Dow Chemical Company, Mich., USA) | From about 20 to about 30; from about 20 to about 25; from about 25 to about 30; from about 22 to about 27; about any of 20, 21, 22, 23, 24, 25, 26, 27, 28, 29 and 30. |
| Microcrystalline cellulose and colloidal silicon dioxide (e.g., ProSolv ® SMCC HD90) | From about 1 to about 20 or about 1 to about 15 or about 1 to about 10 or about 1 to about 5 or about 5 to about 20 or about 5 to about 15 or about 5 to about 10 or about any one of 1, 2, 3, 4, 5, 6, 7, 8, 9 or 10 weight percent. |
| Stearate salt (such as magnesium stearate (e.g., HyQual ®) | From about 0.1 to about 2 or about 0.1 to about 1.5 or about 0.1 to about 1.0 or about .01 to about .09-5 or about 0.1 to about 0.8 or about 0.1 to about 0.7 or about 0.1 to about 0.6 or about 0.1 to about 0.5 or about 0.2 to about 0.8 or about 0.3 to about 0.7 or about 0.4 to about 0.6 or about any one of 0.1, 0.2, 0.3, 0.4, 0.5, 0.6, 0.7, 0.8, 0.9 or 1.0 weight percent. | about 60% w/w, about 35% to about 50% w/w, or about 35% to about 45% w/w, for example about 33% w/w or about 43% w/w An extended release formulation can comprise about 20 to about 50 or about 20 to about 40 or about 20 to about 30% w/w, such as about 25% w/w of a water-swellable, pH independent polymer, for example, hypromellose. An extended release formulation can comprise about 20% to about 25% w/w, such as about 21%, of an anionic, pH-dependent, gel-forming copolymer, for example, an alginate salt like sodium alginate. An extended release formulation can comprise about 1% to about 5% w/w, such as about 4% w/w, of a hydrocolloid polymer, for example, a carrageenen like iota carrageenen. An extended release formulation can comprise about 20% w/w to about 50% w/w, or about 20% w/w to about 40% w/w, or about 20% w/w to about 30% w/w of a hydrogel-forming polymer, for example, a polyethylene oxide.

In one embodiment of the extended release pharmaceutical formulation, the in vitro release profile of sialic acid at intestinal pH is near linear, i.e., substantially a zero order release pattern. The term "intestinal pH" means a pH in the range of about 5.0 to about 7.7. In one embodiment, the intestinal pH means a pH in the range of about 5.5 to about 7.2. In another embodiment, the intestinal pH means a pH in the range of about 6.2 to about 7.0.

Dosage Forms

Extended release formulations can be formulated as solids, semi-solids, liquids, or gases, such as tablets, capsules, powders, granules, ointments, solutions, suppositories, injections, inhalants, gels, microspheres, or aerosols. An extended release pharmaceutical formulation can be formulated for administration by a variety of routes such as oral, parenteral (including subcutaneous, intravenous, intramuscular, and intraperitoneal), rectal, dermal, transdermal, intrathoracic, intrapulmonary, and intranasal (respiratory) routes.

An extended release formulation can be formulated for parenteral administration, for example, by bolus injection, or continuous infusion, and can be formed in unit dose form in ampoules, pre-filled syringes, small volume infusion containers, or in multi-dose containers. An extended release formulation can form suspensions, solutions, or emulsions in oily or aqueous vehicles.

The one or more compounds in the sialic acid biosynthetic pathway or derivative thereof and other ingredients can also be in powder form. Powders can be reconstituted before administration, for example, parentaral injection. Also, powders can be ingested directly, filled inside a capsule such as a gelatin capsule, or formed into a tablet. Such powders can be manufactured by any suitable method, for example, by aseptic isolation of sterile solid or lyophilization from solution.

For topical administration, an extended release formulation can be formulated for direct application to a target area. Dosage forms for topical administration include, for example, one or more of creams, milks, gels, dispersions, microemulsions, lotions, thickened lotions, impregnated pads, ointments, sticks, aerosol formulations (e.g., sprays or foams), soaps, detergents, lotions, cakes of soap, wound dressings, coated bandages, polymer-containing coverings, ointments, creams, lotions, pastes, jellies, sprays, and aerosols. For dermal administration, the extended release pharmaceutical formulation can be delivered directly to the skin, such as by applying a liquid formulation to the skin, or by applying a dressing such as one or more patches or bandages that is impregnated with the formulation. Ointments and creams can, for example, be formulated with an aqueous or oily base with the addition of suitable thickening and/or gelling agents. Drops, such as eye drops or nose drops, can be formulated with the one or more compounds in the sialic acid biosynthetic pathway or derivative thereof in an aqueous or non-aqueous base. Liquid sprays are conveniently delivered by nebulizers. Drops can be delivered by a simple eye dropper-capped bottle, or by a plastic bottle with a closure that is specially adapted to deliver liquid contents dropwise.

For oral administration, an extended release formulation can be in a solid dosage form, such as capsules, tablets, and powders, or in liquid dosage forms, such as elixirs, syrups, and suspension. An extended release formulation can be in unit dosage form, such as a tablet or capsule.

A tablet or capsule can include a coating. The coating can be an enteric coating, which can comprise an acid-resistant coating. The enteric coating can be a time-release coating, such as a coating that degrades at a relatively constant rate until the coatings dissolves sufficiently for the time-release coating to rupture. The time required for the rupture of time-release enteric coatings can depend only on the coating thickness, and can further be largely independent of pH.

Numerous types of acid-resistant enteric coatings are available. Examples of the acid-resistant coatings include cellulose acetate phthalate, polyvinyl acetate phthalate, shellac, an acrylic acid homopolymer or copolymer, a methacrylic acid homopolymer or copolymer, cellulose acetate trimellitate, hydroxypropyl methylcellulose phthalate or a combination of thereof. A number of copolymers of methacrylic acid are known in the art and are commercially available. Examples of such polymers are copolymers of methylmethacrylate and methacrylic acid and copolymers of ethylacrylate and methacrylic acid, and sold under the tradename Eudragit (Rohm GmbH & Co. KG). Examples include Eudragit® L 100-55, Eudragit® L 30D-55, Eudragit® L 100, Eudragit® S100-55 and Eudragit® FS 30D. An enteric coating can also include one or more of titanium dioxide, polydextrose, hypromellose, triacetin, macrogol, and PEG as colorants, plasticisers, and the like. The enteric coating can be present, for example, from about 1% to about 5% w/w of the extended release formulation.

Examples of time-release coatings include, without limitation, cellulose acetate, cellulose acetate butyrate, cellulose acetate propionate, EC, and copolymers of acrylate and methacrylates with quaternary ammonium groups, such as Eudragit® RL, Eudragit® RS, and Eudragit® NE30-D.

An extended release formulation can comprise one or more film coatings. An enteric or non-enteric film coating agent can be used as film coating agents. Enteric film coating agent can include cellulose acetate phthalate (CAP), polyvinyl acetate phthalate (PVAP), a methacrylate polymer (Eudragit L, S), or the like, while the non-enteric film coating agent can include hydroxypropylcellulose (HPC), MC, EC, HPMC, povidone, PVA, CA, shellac, and the like.

Coated tablets or capsules, such as tablets or capsules with one or more enteric coatings, film coatings, time-release coatings, and the like, can be prepared in various sizes. For example, coated tablets can have a length of about 16-20 mm, a width of about 7-12 mm, and a thickness of about 5-8 mm. Some coated tablets have a length of about 17.7 mm, a width of about 9.1 mm, and a thickness of about 6.7 mm. Other coated tablets have a length of about 19.3 mm, a width of about 9.7 mm, and a thickness of about 8.0 mm.

Thus, an extended release formulation can comprise a drug load of about 30% to about 60% w/w, such as about 20% to about 30% w/w of a water-swellable, pH independent polymer, about 20% to about 25% w/w of an anionic, pH-dependent, gel-forming copolymer, about 1% to about 5% w/w of a hydrocolloid polymer, about 1% to about 10% w/w of microcrystalline cellulose and colloidal silicon dioxide, about 0.1% to about 1% w/w magnesium stearate, and, when a coating is present, about 1% to about 5% of the coating, such as an enteric coating. For example, an extended release formulation can comprise a drug load of about 30-60% (e.g., sialic acid and/or ManNAc), about 20% to about 30% w/w hypromellose (e.g. hypromellose Type 2208 or Methocel K100M), about 20% to about 25% w/w sodium alginate (e.g. Protanal), about 1% to about 5% w/w lambda carrageenan (e.g. Viscarin GP-209), about 1% to about 10% w/w of microcrystalline cellulose and colloidal silicon dioxide (e.g., Prosolv® SMCC HD90), about 0.1% to about 1% w/w/magnesium stearate (e.g. HyQual®), and about 1% to about 5% of an enteric coating (e.g. Opadry® II White); or a drug load of about 30-60% (e.g., sialic acid and/or ManNAc), about 25% w/w of a water-swellable, pH independent polymer (e.g. hypromellose), about 21% w/w of an anionic, pH-dependent, gel-forming copolymer (e.g., an alginate salt), about 4% w/w of a hydrocolloid polymer (e.g., a carrageenan), about 5% w/w of microcrystalline cellulose and colloidal silicon dioxide (e.g., Prosolv® SMCC HD90), about 0.5% w/w/magnesium stearate (e.g., HyQual®), and about 3.5% of an enteric coating (e.g., Opadry® II White). In another example, an extended release formulation can comprise a drug load of about 30% to about 60% (e.g., sialic acid and/or ManNAc), about 25% w/w hypromellose (e.g., hypromellose Type 2208 or Methocel K100M), about 21% w/w sodium alginate (e.g. Protanal), about 4% w/w lambda carrageenan (e.g. Viscarin GP-209), about 5% w/w of microcrystalline cellulose and colloidal silicon dioxide (e.g., Prosolv® SMCC HD90), about 0.5% w/w/magnesium stearate (e.g. HyQual®), and about 3.5% of an enteric coating (e.g. Opadry® II White).

An exemplary extended release formulation can comprise a drug load of about 30-60% (e.g., sialic acid and/or ManNAc), about 20% to about 30% w/w, such as about 25%, w/w of a hydrogel-forming polymer (e.g. polyethylene oxide, such as Polyox WSR®); about 20% to about 25% w/w, such as about 21% w/w, of an anionic, pH-dependent, gel-forming copolymer (e.g., an alginate salt, such as sodium alginage); about 1% to about 5 w/w, such as about 4% w/w. of a hydrocolloid polymer (e.g., a carrageenan, such as lambda carrageenan, which is sold as Viscarin GP-209); about 1% to about 10% w/w, such as about 5% w/w of microcrystalline cellulose and colloidal silicon dioxide (e.g., Prosolv® SMCC HD90); about 0. % to about 1% w/w, such as about 0.5% w/w magnesium stearate (e.g. HyQual®); and about 1% to about 5% w/w, such as about 3.5% w/w of an enteric coating (e.g. Opadry® II White).

Extended release dosage forms can be manufactured by methods known in the art. For example, the components of an extended release formulation can optionally be delumped and sieved to a desired particle size before or after they are combined and mixed to provide a uniform or substantially uniform blend. This blend can be used to prepare particular dosage forms, such as tablets or capsules, by known methods, such as direct compression, dry granulation, wet granulation, capsule filling, and the like.

Tablets or capsules can then be coated, although this is not required unless otherwise specified. When coatings, such as enteric coatings, time release coatings, or film coatings are present, they can be applied by conventional means, for example, a pan coating method, a fluidized bed coating method, a compression coating method, and the like.

When various components are blended during the manufacture of an extended release formulation, the blends can have a particle size such that a majority of particles are retained by a 45 µm sieve, for example, the blends can have a particle size such that at least 10%, at least 30%, at least 40%, or at least 50% of the particles are retained by a 45 µm sieve. The blend can be filled into a die (for tablets) or capsule filler (for capsules) for preparation of a batch of unit dosage forms. Each unit dosage form in a batch of unit dosage forms can have the same potency (amount of drug per unit dosage form) within an allowable margin, such as a relative standard deviation (RSD) of less than 8%, less than 7.8%, or less than 6%, depending on the particular requirements of the individual batch.

Methods of Treating and Preventing Sialic Acid Deficiencies

Methods of treating and/or preventing sialic acid deficiencies in an individual in need thereof can include administering an effective amount of one or more compounds in the sialic acid pathway or derivatives thereof in any extended release formulation described herein to the individual in need thereof.

A method of treating an individual with a sialic acid deficiency, or a method of preventing a sialic acid deficiency, can comprise identifying an individual having or likely to develop a sialic acid deficiency by determining genotype or expression levels of the gene GNE.

Sialic acids are important for proper development and functioning of many organs and tissues, and a deficiency of sialic acid can give rise to many different types of diseases and conditions that can be treated, for example, by administration of one or more extended release formulations and dosage forms as described herein to an individual in need thereof.

The diseases and conditions related to sialic acid deficiency can include one or more myopathies and one or more muscle disfunctions, for example, muscular atrophy and/or muscular dystrophy. A method of treating or preventing one or more myopathies can comprise administration of one or more extended release formulations or dosage forms as described herein to an individual in need thereof. The one or more myopathies can be, for example, distal myopathy with rimmed vacuoles (Nonaka myopathy). Methods of treating these myopathies can improve muscle function and/or reduce muscle injury from physical activity. This improvement in function and/or reduction in injury can be quantified by measuring creatine kinase plasma levels after exercise.

A method of treating or preventing muscle dysfunction can comprise administration of one or more extended release formulations and dosage forms as described herein to an individual in need thereof. The muscle dysfunction can include, for example and without limitation, muscular dystrophy hereditary inclusion body myopathy (HIBM). The method can improve one or more of independent ambulation, stair climbing, foot drop, getting up from a chair and walking, hand grip and manipulation and pulmonary function in an individual in need thereof. Methods of improving muscle function in an individual in need thereof can comprise administering an effective amount of one or more compounds in the sialic acid pathway or derivatives thereof.

Methods of treating sialic acid deficiency can treat sialic acid deficiencies related to one or more kidney conditions and/or diseases, for example, kidney diseases and/or conditions involving one or more of proteinuria and hematuria.

Sialic acid deficiencies and conditions related to such deficiencies can be treated or prevented by increasing production of sialic acid. Methods of increasing production of sialic acid, for example of increasing production of sialic acid in muscle tissue, or for increasing the amount of CMP-sialic acid (which can be glycosylated in situ to form sialic acid) in an individual in need thereof can comprise administering an effective amount of one or more compounds in the sialic acid pathway or derivatives thereof.

Sialic acid deficiencies and conditions related to such deficiencies can be treated or prevented by increasing sialylation of substrates, particularly substrates in muscle tissue. Methods of increasing sialylation of substrates in muscle tissue in an individual in need thereof can comprise administering an effective amount of one or more compounds in the sialic acid pathway or derivatives thereof.

Unit Dosages and Articles of Manufacture

Articles of manufacture and unit dosages can comprise one or more extended release formulations, the one or more extended release formulations comprising one or more compounds in the sialic acid pathway or derivatives thereof described herein.

Articles of manufacture or kits can comprise: (a) a container comprising one or more extended release pharmaceutical formulations, the one or more extended release formulations comprising one or more compounds in the sialic acid biosynthetic pathway or derivative thereof; and (b) a package insert with instructions for treating and/or preventing a sialic acid deficiency in a patient. In some embodiments, the one or more compounds in the sialic acid pathway or derivatives thereof include ManNAc or a derivative thereof and/or sialic acid or a derivative thereof.

Example 1

Human myoblasts are obtained from an HIBM patient and grown and differentiated into myotubes. After an appropriate washout, the cells are placed in protein free or sialic acid free medium and then treated with differing concentrations of sialic acid, ManNAc, or both for different periods of time. At time points 0 (before supplementation), 2 hours, 8 hours, 16 hours, and 24 hours after the start (and different times after removal of replacement substrates from each culture), internal sialic acid, CMP-sialic, and glycosylation of newly synthesized proteins are measured. Glycosylation replacement after 24 hours is evaluated and a time course is also determined for glycosylation with replacement, runs out of substrate, and stops glycosylating.

Example 2

Human HIBM myoblasts are obtained and differentiated into myotubes as described in Example 1 and this time, a matrix of sialic acid and N-acetylmannosamine is given for either short bursts of 1-2 hours or longer periods of 4 and 8 hours. The onset of normalization of sialylation and the peak efficiency is evaluated, as well as the time to decline of normal sialylation. Efficacy of single and combination formulations in replacement treatment and effective time are determined.

Example 3

A large variety of human fibroblasts from HIBM patients are obtained with different mutations and clinical phenotypes. Each line is titrated to its 50% maximal correction with sialic acid and ManNAc independently. Replacement efficacy is evaluated for different lines from different patients.

Example 4

A mouse model of HIBM is treated with either standard sialic acid or ManNAc or given both compounds together. An additional group is given these items in an extended release formulation. The mice are evaluated using the procedure described in Malicdan et al., *Nat. Medicine* 15(6):690-695 (2009) for muscle strength and clinical outcome. In addition, mice are analyzed at different time points after a dose and during treatment to assess glycosylation and intermediates in the muscle tissues. Clinical effect and the best steady state restoration of intermediates are evaluated.

Example 5

To assess the minimal concentration of sialic acid metabolite required to maintain sialylation optimally, myoblasts, myotubes or human fibroblasts are cultured in sialic acid free medium until they reach an abnormal level of sialylation at steady state. A series of concentrations to these cultures are added and evaluated for the restoration of glycosylation. Concentration in the medium required at steady state to replace the missing sialylation is determined. This concentration provides a target for a minimum plasma concentration within patients treated with an extended release formulation.

Example 6

Preparation of Sialic Acid 250 mg Strength Tablets Using Dry Blend Method of Manufacture Experimental/Materials Sialic Acid (Food & Bio Research center, Inc. Kyoto Japan) was stored in aluminum foil bags at −20 C. However, handling and processing of prototypes were all under ambient room temperature. In-process materials and bulk tablets were stored in double polyethylene bags with desiccant. The sialic acid was evaluated for physical properties consisting of morphology, particle size by sieve analysis, bulk and tap density.

50 gram lab-scale batches were prepared using bag-blending, manual filling and hand turning of the tablet press to compress tablets to evaluate dissolution as the first level of screening. Tablets were manufactured using the extended release platform of the present invention. Their formulas are listed below in Table 1 and 2.

TABLE 1

Quantitative Extended Release Formula for Sialic Acid, Hypromellose 250 mg Tablets:

| Ingredient | Vendor | mg/Tablet | % w/w | g/batch |
|---|---|---|---|---|
| Sialic Acid (N-Acetylneuraminic acid) | Food and BioResearch Center, Inc | 249.75 | 33.3 | 16.65 |
| Hypromellose, Type 2208 (Methocel ® K100 M Premium CR) | Colorcon | 225.0 | 30.0 | 15.0 |
| Sodium Alginate (Protanal ® LF 120M) | FMC Biopolymer | 187.5 | 25.0 | 12.5 |
| Carrageenan (Viscarin GP-209) | FMC Biopolymer | 37.5 | 5.0 | 2.5 |
| Microcrystallline Cellulose and Colloidal Sillicon Dioxide (ProSolv ® SMCC HD 90) | JRS Pharma | 46.5 | 6.2 | 3.1 |
| Magnesium Stearate (HyQual ®), Vegatable Source Product Code 2257 | Mallinckrodt | 3.75 | 0.5 | 0.25 |
| Total | | 750 | 100% | 50 |

TABLE 2

Quantitative Extended Release Formula for Sialic Acid Polyox, 250 mg Tablets:

| Ingredient | Vendor | mg/ Tablet | % w/w | g/ batch |
|---|---|---|---|---|
| Sialic Acid (N-Acetylneuraminic acid) | Food and BioResearch Center, Inc | 249.75 | 33.3 | 16.65 |
| Polyethylene Oxide WSR (Polyox) | Dow Chemical Company | 225.0 | 30.0 | 15.0 |
| Sodium Alginate (Protanal ® LF 120M) | FMC Biopolymer | 187.5 | 25.0 | 12.5 |
| Carrageenan (Viscarin GP-209) | FMC Biopolymer | 37.5 | 5.0 | 2.5 |
| Microcrystallline Cellulose and Colloidal Sillicon Dioxide (ProSolv ® SMCC HD 90) | JRS Pharma | 46.5 | 6.2 | 3.1 |
| Magnesium Stearate (HyQual ®), Vegatable Source Product Code 2257 | Mallinckrodt | 3.75 | 0.5 | 0.25 |
| Total | | 750 | 100 | 50 |

Sialic Acid, hypromellose Type 2208, sodium alginate, carrageenan and microcrystalline cellulose with colloidal silicon dioxide were delumped using a #20 USA standard sieve and weighed per the quantitative formula. The ingredients were combined in a small ziplock bag and blended for 15 minutes. Magnesium stearate was delumped using a #40 USA standard screen, weighed per quantitative formula, and added to the blended ingredients in the bag. The ingredients were blended for an additional three minutes. The final blends, as well as the un-sieved sialic acid were characterized using bulk density, tap density, particle size sieve analysis, Carr's Compressibility Index, and minimum critical orifice. The final blend of each prototype was compressed on the Korsch PH100 tablet press. The resulting tablets were submitted to the analytical lab for dissolution testing.

Sialic Acid Characterization

Figure 2:
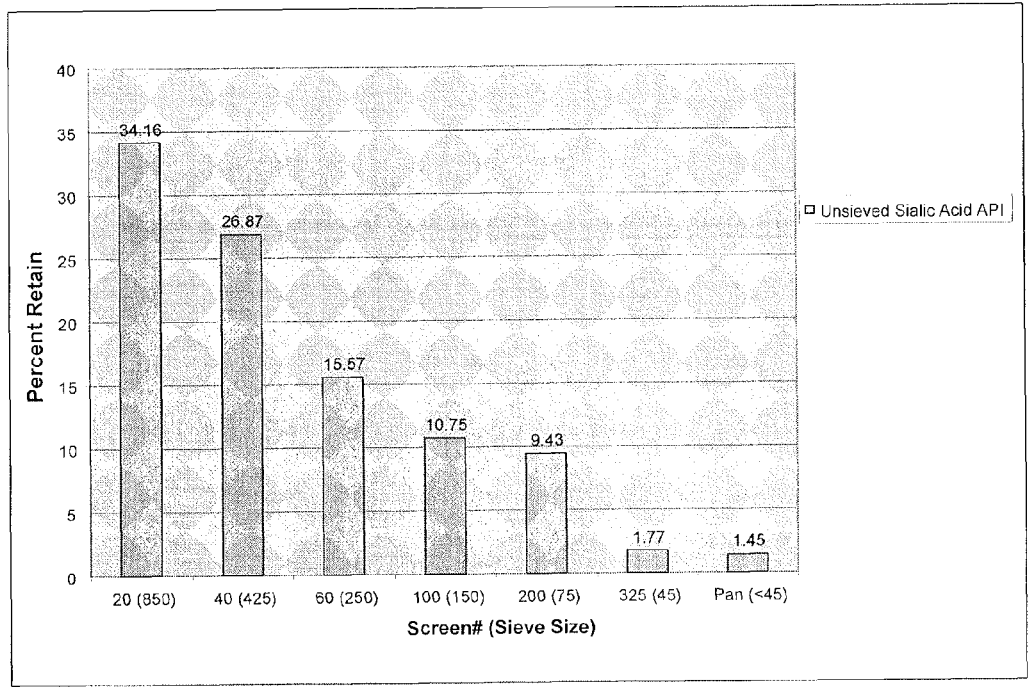
FIG. 2 is a graph of an exemplary particle size distribution for sialic acid.

Sialic Acid was visually characterized as a white fluffy powdery substance. Its bulk density was 0.293 g/mL, and its tap density was 0.419 g/ml. The Carr's Compressibility Index was 30%, and the minimum critical orifice diameter was 18 mm. The particle size sieve analysis of Sialic Acid (Table 3) revealed a distribution of coarse and midsize particles as shown in FIG. 2. The sialic acid was sized prior to blending to facilitate blend homogeneity.

TABLE 3

Particle Size Distribution for Sialic Acid

| Sieve #(Mesh size (um)) | Unsieved Sialic Acid (N-Acetylneuraminic acid) |
|---|---|
| 20 (850) | 34.16 |
| 40 (425) | 26.87 |
| 60 (250) | 15.57 |
| 100 (150) | 10.75 |
| 200 (75) | 9.3 |
| 325 (45) | 1.77 |
| Pan (<45) | 1.45 |

Extended Release Sialic Acid, 250 mg CR Tablets

Figure 3:
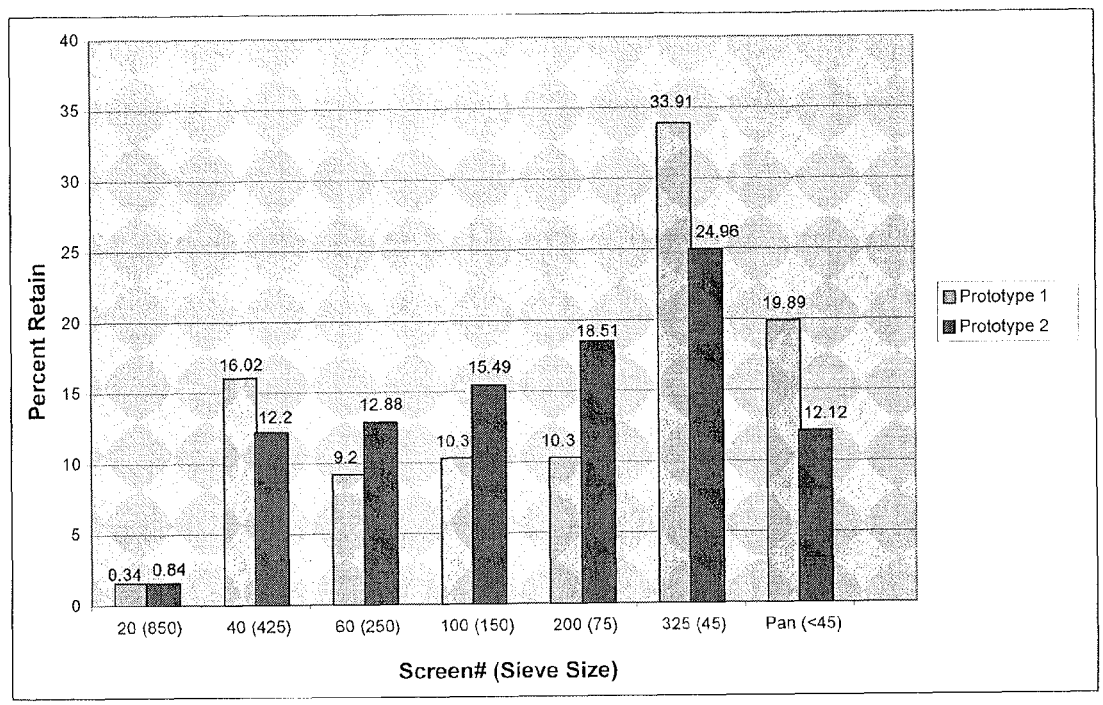
FIG. 3 is a graph of an exemplary particle size distribution plot for extended release sialic acid 250 mg formulation blends.

Both prototype blends, Extended Release hypromellose and Extended Release Polyox, were compressed into tablets using 0.3300×0.7100 inch modified oval tooling targeting a tablet weight of 750 mg and a hardness range of 17 to 20 Kp. During tableting, powder bridging in the die cavity was observed for extended release hypromellose. This was an indication that the blend needed to be densified to improve flowability on the tablet press. Extended release Polyox appeared denser and seemed to flow better on the tablet press. However, its Carr's Compressibility Index and minimum critical orifice diameter results, as shown in Table 4, indicated that it also needed further processing such as, granulation. The particle size distribution of the Polyox prototype seemed to be more dispersed over various screen sizes than the hypromellose prototype shown in Table 5 and FIG. 3.

TABLE 4

Physical Characterization Results of Sialic Acid 250 mg

| Powder | Bulk Density (g/mL) | Tap Density (g/mL) | Carr's Compressibility Index (%) | Flodex Critical Orifice (mm) |
|---|---|---|---|---|
| Sialic Acid (N-Acetylneuraminic acid) | 0.293 | 0.419 | 30 (poor flow) | 18 |
| Prototype 1 (Hypromellose) | 0.359 | 0.543 | 33.8 (very poor flow) | 20 |
| Prototype 2 (Polyox) | 0.439 | 0.716 | 38.7 (very very poor flow) | 18 |

TABLE 5

Particle Size Distribution for Extended Release Sialic Acid, 250 mg Tablets.

| Sieve #(Mesh size (um)) | Prototype 1 with Hypromellose % Retain | Prototype 2 with Polyethylene oxide % Retain |
|---|---|---|
| 20 (850) | 0.34 | 0.84 |
| 40 (425) | 16.02 | 15.20 |
| 60 (250) | 9.2 | 12.88 |
| 100 (150) | 10.3 | 15.49 |
| 200 (75) | 10.3 | 18.51 |
| 325 (45) | 33.91 | 24.96 |
| Pan (<45) | 19.89 | 12.12 |

Figure 4:
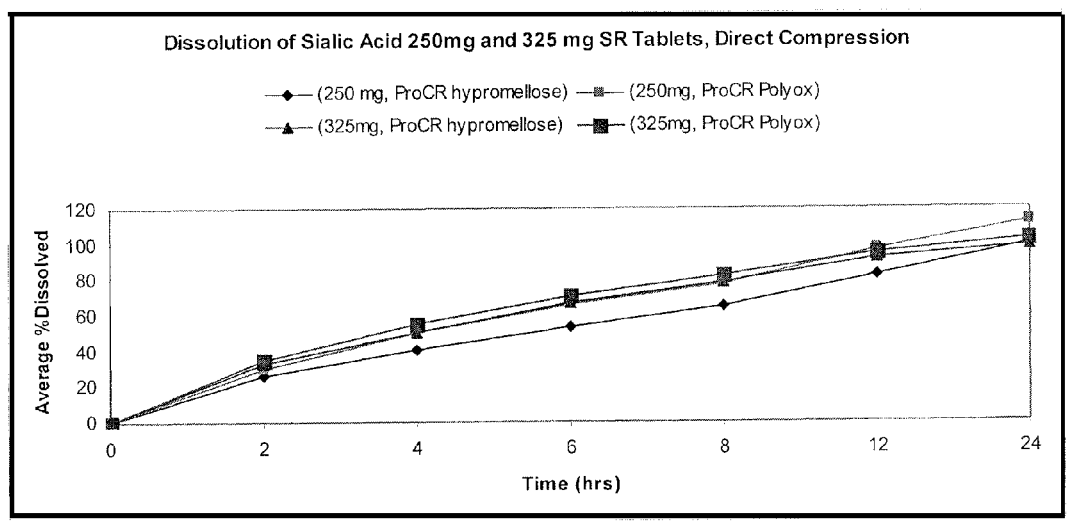
FIG. 4 is a an exemplary dissolution profile of sialic acid 250 and 325 mg extended release (ER) tablets formed by direct compression.

The compression of the tablets resulted in a weight range of 3-5% of the target of 750 mg. The variability was primarily due to the manual filling and poor flow. Regardless of the weight variability, the tablet appearance and hardness was good, ranging from 13 to 18 Kp, as listed in Table 6. The dissolution results showed a first order sustained release profile over a 12 hour period, as shown in Table 7 and FIG. 4. The dissolution method was outlined as follows:

Sample volume: 900 mL;

Apparatus: USP 1 (Baskets);

Dissolution medium: 50 mM Phosphate, pH 6.8;

Basket speed: 100 RPM;

Pull volume: 10 mL; and

Temperature: 37° C.

Figure 5:
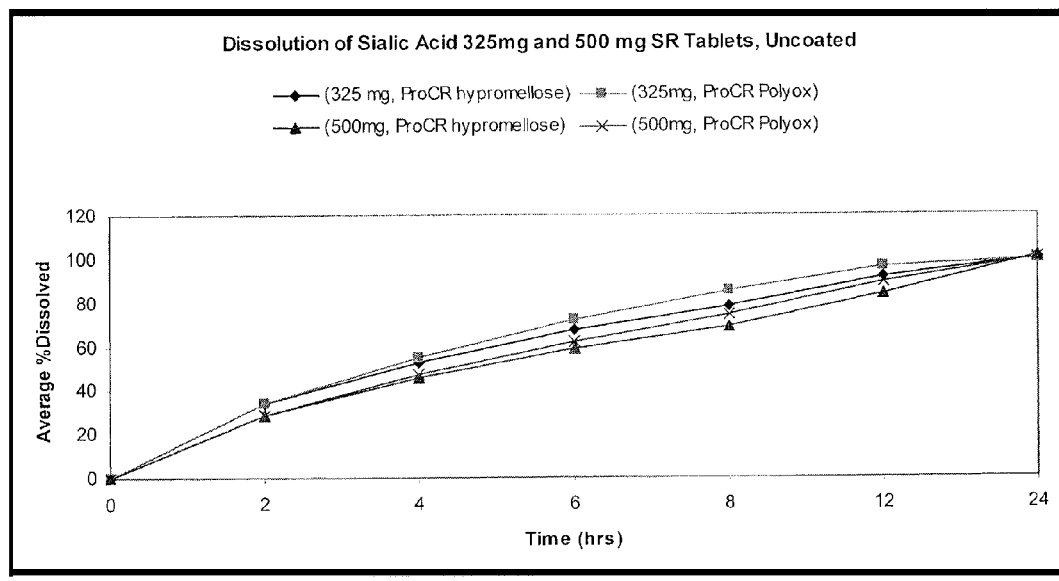
FIG. 5 is an exemplary dissolution profile of sialic acid 325 mg and 500 mg extended release (ER) uncoated tablets.
Figure 6:
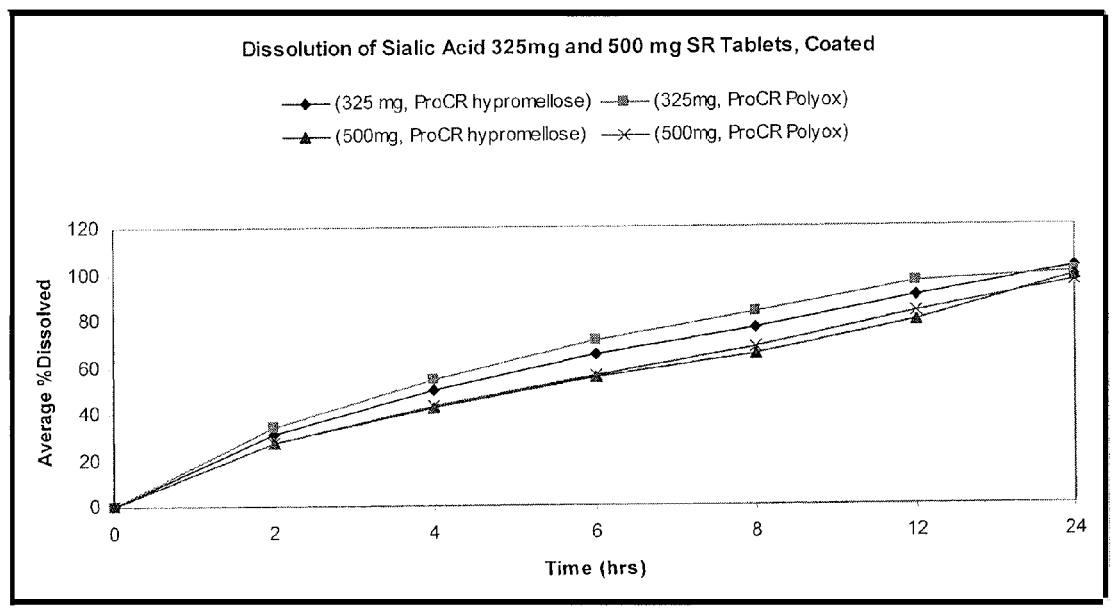
FIG. 6 is an exemplary dissolution profile of sialic acid 325 mg and 500 mg extended release (ER) coated tablets.

The above same dissolution method was also used for the dissolution tests resulting in FIGS. 5 and 6.

TABLE 6

Physical Data of Sialic Acid 250 and 325 mg Tablets

| Test | Hypromellose 250 mg Tablets | Polyox 250 mg Tablets | Hypromellose 325 mg Tablets | Polyox 325 mg Tablets |
|---|---|---|---|---|
| Tablet Weight (mg) | 744-787 | 746-751 | 747-766 | 745-771 |
| Tablet Thickness (in) | 0.268-0.271 | 0.261-0.263 | 0.291-0.295 | 0.283-0.286 |
| Tablet Hardness (kp) | 17.5 | 18.3 | 13.2 | 13.0 |
| Tablet Friability (%) | ND | ND | ND | ND |

ND: Not determined

TABLE 7

Dissolution Results of Direct Compression Prototypes

| Test | Hypromellose 250 mg Tablets | Polyox 250 mg Tablets | Hypromellose 325 mg Tablets | Polyox 325 mg Tablets |
|---|---|---|---|---|
| Dissolution (Average n = 3) % Release | | | | |
| 2 hr | 26 | 30 | 33 | 35 |
| 4 hr | 41 | 50 | 50 | 55 |
| 6 hr | 53 | 66 | 67 | 71 |
| 8 hr | 65 | 77 | 78 | 82 |
| 12 hr | 82 | 97 | 92 | 95 |
| 16 hr* | — | — | 99 | 103 |
| 24 hr | 100 | 112 | — | — |

*Represented as last time point in graph

Example 7

Preparation of Sialic Acid 325 and 500 mg Development Prototypes

Initially, two small 50 gram dry blend batches were manufactured with an increased drug load from 33% w/w to 43% w/w to verify that the drug release profile was acceptable. The two compositions are listed in Table 8 as hypromellose and Polyox. The tabletting was done as described before using a manual fill into the die cavity.

TABLE 8

Quantitative Formula for Sialic Acid 325 mg and 500 mg Extended release Tablets Prototypes:

| Ingredient | Vendor | mg/Tablet Hypromellose | mg/Tablet Polyox | % w/w | g/batch 50 g size | g/batch 1800 g size |
|---|---|---|---|---|---|---|
| Sialic Acid (N-Acetylneuraminic acid) | Food and BioResearch Center, Inc | 325.0 | 325.0 | 43.3 | 21.65 | 779.4 |
| Hypromellose, Type 2208 (Methocel ® K100 M Premium CR) | Colorcon | 191.3 | — | 25.5 | 12.75 | 459 |
| Polyethylene Oxide WSR (Polyox) | | — | 191.3 | 25.5 | 12.75 | 459 |
| Sodium Alginate (Protanal ® LF 120M) | FMC Biopolymer | 159.0 | 159.0 | 21.2 | 10.60 | 381.6 |
| Carrageenan (Viscarin GP-209) | FMC Biopolymer | 31.5 | 31.5 | 4.2 | 2.10 | 75.6 |
| Microcrystallline Cellulose and Colloidal Sillicon Dioxide (ProSolv ® SMCC HD 90) | JRS Pharma | 39.8 | 39.8 | 5.3 | 2.65 | 95.4 |
| Magnesium Stearate (HyQual ®), Vegatable Source Product Code 2257 | Mallinckrodt | 3.8 | 3.8 | 0.5 | 0.25 | 9.0 |
| Total for 325 mg Strength | | 750.4 | 750.4 | 100 | 50 | 1800 |
| Total for 500 mg Strength | | 1154.5 | 1154.8 | 100 | — | — |

Wet Granulation Method of Manufacture

In order to avoid bridging and poor flow during compression batch sizes were scaled up from 50 grams to 1800 grams, and a high shear granulation method of manufacture was used to produce 325 and 500 mg dose strengths while maintaining good tablet compression properties. The 325 and 500 mg dose strengths shared a common blend that was divided prior to compression. Two tablet sizes were produced: A 325 mg dose strength tablet with a length of 17.7 mm, a width of 9.1 mm and a thickness of 6.7 mm; and a 500 mg dose strength tablet with a length of 19.3 mm, a width of 9.7 mm and a thickness of 8.0 mm). The following equipment and process were used to make these tables.

Experimental/Materials

All raw materials were used as received from vendors as listed in Table 8. The batch size was 1800 grams. The following equipment was used:

Fielder PP1 High Shear Granulator
Niro-Aeromatic MP-1 Multi-processor
FitzMill JT Homoloid equipped with knives forward, 0.079" round hole screen
4 Qt PK Blender
Korsch PH100 tablet Press equipped with 0.350"×0.6875" modified oval tooling for the 750 mg tablet and 0.374"×0.7480" modified oval tooling for the 1154 mg tablet
Accela-cota model 24MK III (24" coating pan)

All the raw materials with exception of magnesium stearate were charged to the PP-1 granulator and premixed for 3 minutes at 300 rpm impeller speed, no chopper. A baseline loss on drying determination was performed and the ungranulated hypromellose formula was determined to be 3.4% water while the Polyox formulation was 2.9%. Water was sprayed at approximately 200 grams/minute while mixing at 300 rpm with a slow chopper speed. The hypromellose formulation used 43% water (778 g water sprayed) of the 1.8 kg batch size while the Polyox formulation sprayed 52% water (905 g water sprayed) with a 2 minute post spray mix. The granulation was transferred into the MP-1 fluid bed and dried with an inlet temperature of 75° C. until the loss on drying (LOD) was ≤3%; equal to or slightly lower than the baseline moisture of the un-granulated formulations. The dried granulation was passed through a #4 mesh hand screen. The large granules retained on the #4 mesh were segregated and discarded. The remaining granules were sized through the FitzMill at low speed, knives forward. The blend was then lubricated with the magnesium stearate for 3 minutes. The final blend was compressed into tablets using a Korsch rotary press. After dissolution results were obtained, the core tablets were coated with a non-functional, Opadry II, white to a weight gain of approximately 4.5% w/w.

Outline of Dissolution Conditions were as follows:
Sample volume: 900 mL;
Apparatus: USP 1 (Baskets);
Dissolution medium: 50 mM Phosphate, pH 6.8;
Basket speed: 100 RPM;
Pull volume: 10 mL;
Temperature: 37° C.; and
Time points: 2, 4, 6, 8, 12, 16 or 24 hours.

The blending and granulation of the hypromellose based formulation proceeded smoothly. The hypromellose formulation processed well, producing a final blend with excellent flow that compressed well on the tablet press. The yield was excellent (96%) for a small scale batch size.

The Poly Ethylene Oxide (Polyox) based formulation did not granulate as easily. The Polyox formulation was over-granulated. The over-granulation can be alleviated in the future by spraying less granulation water at a slower rate. An appreciable amount of the granulation was lost when the partially dried granulation was screened through a 4 mesh sieved to remove large over-granulated agglomerates that resisted drying in the fluid bed. As a result, the batch yield was poor at 83%. The portion of the batch that was retained produced an excellent final blend, however. It flowed and compressed well on the tablet process and produced good quality tablets. Polyox is known for being difficult to granulate so this is not entirely unexpected. However, with the proper granulation parameters an excellent granulation can be attained.

Physical data for sialic acid 325 mg final blends, sialic acid 325 mg tablets, and sialic acid 500 mg tablets are shown in Tables 9, 10 and 11, respectively. Analytical results for sialic acid 325 and 500 mg tablets (uncoated) are shown in Table 12.

TABLE 9

Physical data for Sialic Acid, 325 mg Final Blends:

|  | (Hypomellose) | (Polyox) |
|---|---|---|
| Sieve # (% Retain) Mesh size (um) | | |
| 14 (1400) | 0.10 | 1.32 |
| 30 (600) | 42.89 | 45.4 |
| 40 (425) | 12.28 | 14.39 |
| 140 (106) | 33.98 | 29.89 |
| 200 (75) | 5.42 | 3.24 |
| 325 (45) | 4.61 | 4.86 |
| Pan (<45) | 0.72 | 0.91 |
| Blend Bulk Density (g/mL) | 0.54.9 | 0.54.5 |
| Tap Density (g/mL) | 0.646 | 0.619 |
| % Compressibility | 15 | 12 |
| Flowdex | 10 | 6 |

TABLE 10

Physical Data of Sialic Acid 325 mg Tablets at Various Hardnesses

| Test | Formulation A | Formulation B Hypromellose | Formulation C | Formulation D | Formulation E Polyox | Formulation F |
|---|---|---|---|---|---|---|
| Tablet Hardness Level | Low | Medium | High/max | Low | Medium | High/max |
| Ave. Weight (mg) | 759.5 | 754 | 754 | 739 | 745 | 750 |
| Ave. Thickness (in) | 0.279 | 0.270 | 0.259 | 0.260 | 0.247 | 0.253 |
| Ave. Hardness (kp) | 6.5 | 10.0 | 14.4 | 9.5 | 17.9 | 15.7 |
| Ave. Friability (%) | Failed | 0.2 | 0.1 | 0.1 | 0.0 | 0.2 |

Note:
Average of 10 tablets

TABLE 11

Physical Data of Sialic Acid 500 mg Final Blends and Tablets

| Test | Formulation G | Formulation H Hypromellose | Formulation I | Formulation J | Formulation K Polyox | Formulation L |
|---|---|---|---|---|---|---|
| Bulk Density (g/mL) | | 0.55 | | | 0.54 | |
| Tablet Hardness Level | Low | Medium* | High/max | Low | Medium | High/max |
| Ave. Weight (mg) | 1170 | ND | 1152 | 1158 | 1154 | 1160 |
| Ave. Thickness (in) | 0.324 | ND | 0.315 | 0.310 | 0.307 | 0.297 |
| Ave. Hardness (kp) | 11.3 | ND | 13.2 | 12.9 | 14.0 | 20.2 |
| Ave. Friability (%) | 0.2 | ND | 0.0 | 0.1 | 0.0 | 0.0 |

Note:
Average of 10 tablets
*ND: not determined

TABLE 12

Analytical Results or Sialic Acid 325 mg and 500 mg Extended Release Tablets (Uncoated)

| Test | Formulation C Hypromellose | Formulation F Polyox | Formulation I Hypromellose | Formulation K Polyox |
|---|---|---|---|---|
| Tablet Strength (mg) | 325 | 325 | 500 | 500 |
| Assay (% LC) | 96.3 | 97.8 | | |
| Impurities (%) | Total: 0.2 | Total: 0.2 | | |
| Dissolution (Average n = 3) % Release | | | | |
| 2 hr | 34 | 34 | 29 | 29 |
| 4 hr | 53 | 55 | 46 | 47 |
| 6 hr | 67 | 72 | 59 | 62 |
| 8 hr | 78 | 85 | 69 | 74 |
| 12 hr | 91 | 96 | 84 | 89 |
| 24 hr | 100 | 99 | 101 | 100 |

The dissolution results (FIG. 5) showed a first order sustained release profile over a 12 hour period for both dose strengths and for both Extended Release hypromellose and Extended Release Polyox. Additionally, these results indicate that the dose proportional approach was successful in providing dose flexibility using a common blend at 750 and 1154 tablet final weights.

Example 8

Coating for Sialic Acid 325 and 500 mg Extended Release Tablets Hypromellose and Polyox Method of Manufacture Eight kilograms of core tablets (approximately 1.5 kg of active tablets combined with 6.5 kg of "sham" placebos to provided volume) were charged into an Accela-Cota coating equipment equipped with a 24" coating pan and two spray guns. The non-functional film coat was Opadry-II White (Colorcon Corporation formula Y-22-7719) at a 20% solids concentration. The purpose of the film coat was to improve aesthetics and in the future facilitate patient compliance for swallowing of the tablet. The target end-point was 3-5% weight gain.

The coating process parameters were as follows:
Pan speed: Target 12-16 rpm
Inlet temperature: 70-85° C.
Outlet temperature: 39-42° C.
Bed temperature: 33-45° C.
Atomization pressure: 40 psi
Spray Rate: 50-60 g/min
Airflow: approximately 200 cfm
Gun to bed distance: 5"

The tablets coated well with no difficulties. Approximately 4% weight gain of coating was sufficient to provide good coverage of the tablet cores.

Prototype Stability

The white film coated tablets of Sialic Acid prepared using Extended Release hypromellose and Extended Release Polyox at 325 mg and 500 mg dose strengths were packaged in thirty (30) units per bottle, one MiniPax desiccant, no coil and induction sealed using a Lepak Jr™ induction cap sealing system. Table 13 lists the packaging components used. All the acceptable tablets were packaged and placed on a 12 month prototype stability program under ICH conditions testing the stability at both 25° C. and 60% relative humidity (RH) and 40° C. and 75% RH at 0, 1, 3, 6, and 12 months. The tablets have been tested and monitored with respect to appearance, dissolution, moisture, assay and related substances, and initial stability results are shown in Table 14. The dissolution profile for the coated 325 mg and 500 mg tablets is shown in FIG. 6.

TABLE 13

List of Packaging Components

| Component | Material Description | AAI RM # |
|---|---|---|
| Bottle | 100 cc Round White HDPE (38/400) | PC-3714 |
| Closure | 38 mm CRC w Foil Seal MI Liner | PC-3982 |
| Desiccant | MiniPax w 1.00 g Silica Gel-Packet | PC-2637 |

TABLE 14

Analytical Results of Sialic Acid 325 mg and 500 mg
EXTENDED RELEASE Tablets (Coated), Initial Stability

| Test | Formulation C Hypromellose | Formulation F Polyox | Formulation I Hypromellose | Formulation K Polyox |
|---|---|---|---|---|
| Tablet Strength (mg) | 325 | 325 | 500 | 500 |
| % Moisture by Karl Fischer | 1.0 | 3.3 | 2.0 | 3.7 |
| Content Uniformity (Ave, n = 10) | 100.0 | 95.6 | 99.8 | 98.6 |
| % RSD | 1.5 | 2.5 | 1.5 | 2.6 |
| AV | 3.5 | 9.2 | 3.6 | 6.3 |
| Assay (% LC) | 100.6 | 97.8 | 98.8 | 96.9 |
| Impurities (%) | Total: <0.10 | Total: <0.10 | Total: <0.10 | Total: <0.10 |
| Dissolution (Ave. % Release, n = 6)) | | | | |
| 2 hr | 31 | 34 | 27 | 27 |
| 4 hr | 50 | 54 | 42 | 43 |
| 6 hr | 65 | 70 | 55 | 56 |
| 8 hr | 75 | 83 | 65 | 68 |
| 12 hr | 90 | 96 | 79 | 83 |
| 24 hr | 102 | 100 | 98 | 96 |

The formulation development activities successfully identified two distinct Extended release prototypes for Sialic Acid in 325 and 500 mg dose strengths. The in-vitro dissolution release profile exhibited a first order release over 12 hours in aqueous medium and pH of 6.8. The Extended release platform was employed. This unique combination of inert polymers provides a robust formulation that is pH independent and lends itself to granulation processes without affecting the dissolution release profile. This was the case for Sialic Acid 325 and 500 mg dose strength EXTENDED RELEASE tablets where a wet granulation process was found necessary to achieve densification and good tablet compressibility.

With regard to chemical stability Sialic Acid 325 and 500 mg hypromellose and Polyox Extended Release tablets showed acceptable assay, dissolution and content uniformity and easily passed USP testing criteria. These prototypes are monitored through a 12 month ICH stability study.

As shown in FIGS. 5 and 6, the dissolution profiles of Sialic Acid hypromellose and Polyox uncoated and coated tablets are consistent. There is no significant change in the sustained release profile over the 12 hour release with the application of Opdary® II White film coat. The analytical results for assay and related substances are acceptable which indicates that the wet granulation, drying and coating processes have no impact on the chemical integrity of the drug.

Example 9

Preparation of ManNAc 325 mg Development Prototypes

Figure 7:
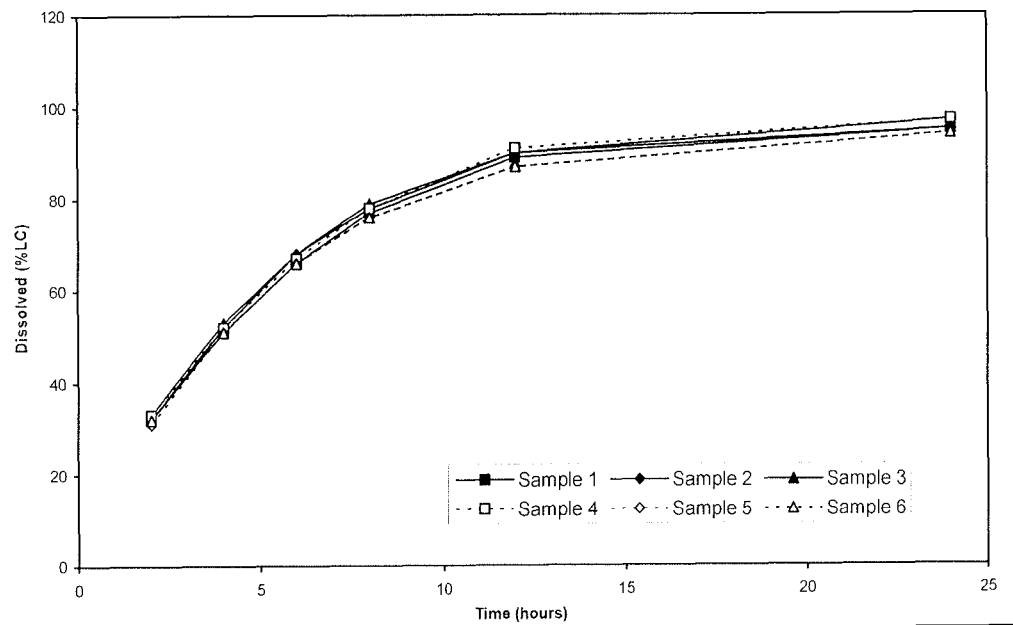
FIG. 7 is an exemplary dissolution profile of ManNAc 325 mg tablets and associated data.

The ManNAc title formulation was prepared according to the method detailed above for Sialic Acid. The dissolution profile of ManNAc 325 mg Tablets is shown in FIG. 7.
Core Tablet Results

| Assay | |
|---|---|
| % LC = | 93.5% |

| Impurity | % RS |
|---|---|
| Sialic Acid | <0.10% |
| Sodium Pyruvate | <0.10% |

-continued

| N-Acetyl-D-Glucosamine | 0.4% |
|---|---|
| Acetic Acid | <0.10% |
| Total | 0.4% |

| KF | |
|---|---|
| Prep | % water |
| 1 | 3.5 |
| 2 | 3.3 |
| Mean(2) | 3.4 |

| Content Uniformity | |
|---|---|
| Unit | % LC |
| 1 | 93.7 |
| 2 | 94.6 |
| 3 | 92.8 |
| 4 | 92.8 |
| 5 | 94.6 |
| 6 | 92.9 |
| 7 | 96.0 |
| 8 | 95.4 |
| 9 | 92.5 |
| 10 | 91.5 |
| Mean (10) | 93.7 |
| % RSD | 1.5 |
| SD | 1.42735186 |
| AV | 8.2 |

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

I claim:

1. An extended release pharmaceutical formulation in oral unit dosage form comprising
   about 43.3% w/w of N-acetylneuraminic acid (NeuAc) or a pharmaceutically acceptable salt thereof;
   about 25.5% w/w of hypromellose or about 25.5% w/w of polyethylene oxide;
   about 21.2% w/w of sodium alginate; and
   about 4.2% w/w of carrageenan;
   wherein the in vitro dissolution release profile of the formulation at intestinal pH is near linear, and the formulation contains about 325 mg to about 500 mg of NeuAc in each unit dosage and provides a steady plasma concentration of NeuAc upon three or four times of oral administration in 24 hours.

2. The extended release pharmaceutical formulation of claim 1, further comprising about 1% to about 10% of a mixture of microcrystalline cellulose and colloidal silicon dioxide.

3. The extended release pharmaceutical formulation of claim 1, further comprising about 0.1% to about 1% of one or more lubricants.

4. The extended release pharmaceutical formulation of claim 3, wherein the one or more lubricants comprise magnesium stearate.

5. The extended release pharmaceutical formulation of claim 1, comprising
   about 43.3% w/w of N-acetylneuraminic acid (NeuAc) or a pharmaceutically acceptable salt thereof;
   about 25.5% w/w hypromellose;
   about 4.2% w/w carrageenan; and
   about 21.2% w/w sodium alginate.

6. The extended release pharmaceutical formulation of claim 5, further comprising
   about 1% to about 10% w/w of the mixture of microcrystalline cellulose and colloidal silicon dioxide; and
   about 0.1% to about 1% w/w magnesium stearate.

7. The extended release pharmaceutical formulation of claim 1, comprising
   about 43.3% w/w of N-acetylneuraminic acid (NeuAc) or a pharmaceutically acceptable salt thereof;
   about 25.5% w/w of polyethylene oxide;
   about 4.2% w/w carrageenan; and
   about 21.2% w/w sodium alginate.

8. The extended release pharmaceutical formulation of claim 7, further comprising
   about 1% to about 10% w/w of the mixture of microcrystalline cellulose and colloidal silicon dioxide; and
   about 0.1% to about 1% w/w magnesium stearate.

9. A method for treating a sialic acid deficiency in an individual in need thereof comprising administering an effective amount of N-acetylneuraminic acid (NeuAc) or a pharmaceutically acceptable salt thereof, in the extended release formulation of claim 1.

10. The method of claim 9, wherein the sialic acid deficiency is a myopathy associated with sialic acid deficiency.

11. The method of claim 10, wherein the myopathy associated with sialic acid deficiency is Hereditary Inclusion Body Myopathy (HIBM), Nonaka myopathy, and/or Distal Myopathy with Rimmed Vacuoles (DMRV).

12. The extended release pharmaceutical formulation of claim 6, wherein the unit dosage form is a tablet or capsule.

* * * * *

UNITED STATES PATENT AND TRADEMARK OFFICE
CERTIFICATE OF CORRECTION

| | | |
|---|---|---|
| PATENT NO. | : 9,241,896 B2 | Page 1 of 1 |
| APPLICATION NO. | : 13/659540 | |
| DATED | : January 26, 2016 | |
| INVENTOR(S) | : Emil Kakkis | |

It is certified that error appears in the above-identified patent and that said Letters Patent is hereby corrected as shown below:

In the Title page (page 1) Item 56, right column, second reference recited under the heading "OTHER PUBLICATIONS", replace "International Search Report and Written Opinion for International U.S. Appl. No. PCT/US2012/061737, mailed Mar. 15, 2013."

with

-- International Search Report and Written Opinion for International Appl. No. PCT/US2012/061737, mailed Mar. 15, 2013. --

Signed and Sealed this
Nineteenth Day of April, 2016

Michelle K. Lee
*Director of the United States Patent and Trademark Office*